(12) United States Patent
Okuno et al.

(10) Patent No.: US 10,132,757 B2
(45) Date of Patent: Nov. 20, 2018

(54) SUBSTRATE PROCESSING DEVICE

(75) Inventors: Masanori Okuno, Toyama (JP); Hisaki Kataoka, Toyama (JP); Tomoyuki Miyada, Toyama (JP)

(73) Assignee: HITACHI KOKUSAI ELECTRIC INC., Tokyo (JP)

( * ) Notice: Subject to any disclaimer, the term of this patent is extended or adjusted under 35 U.S.C. 154(b) by 864 days.

(21) Appl. No.: 14/128,804

(22) PCT Filed: Jun. 18, 2012

(86) PCT No.: PCT/JP2012/065493
§ 371 (c)(1),
(2), (4) Date: Mar. 10, 2014

(87) PCT Pub. No.: WO2012/176727
PCT Pub. Date: Dec. 27, 2012

(65) Prior Publication Data
US 2014/0176701 A1    Jun. 26, 2014

(30) Foreign Application Priority Data

Jun. 24, 2011 (JP) ................................. 2011-140942
Apr. 5, 2012 (JP) ................................. 2012-086743

(51) Int. Cl.
*G01N 21/88*   (2006.01)
*H01L 21/67*   (2006.01)
*H01L 21/677*  (2006.01)

(52) U.S. Cl.
CPC ... *G01N 21/8803* (2013.01); *H01L 21/67288* (2013.01); *H01L 21/67742* (2013.01)

(58) Field of Classification Search
CPC ......... H01L 21/67196; H01L 21/67294; H01L 21/677; H01L 21/67742; H01L 21/67745;
(Continued)

(56) References Cited

U.S. PATENT DOCUMENTS 6,215,897 B1 * 4/2001 Beer ..................... H01L 21/681
                                                      348/87
6,847,730 B1 * 1/2005 Beer ..................... H01L 21/681
                                                      348/125

(Continued)

FOREIGN PATENT DOCUMENTS

JP    06-100202 A    4/1994
JP    08-045806 A    2/1996
(Continued)

*Primary Examiner* — Anand S Rao
*Assistant Examiner* — Samuel D Fereja
(74) *Attorney, Agent, or Firm* — Volpe and Koenig, P.C.

(57) ABSTRACT

Image data pertaining to substrate transfer is efficiently collected and stored for use in analyzing transfer errors. A substrate processing device includes a first control part for stopping a transfer part upon detecting a transfer error in the transfer part for transferring a substrate; a storage part for storing substrate transfer operations of the transfer part as image data; and a second control part for accumulating the image data in an accumulation part at a predetermined period. The first control part obtains information indicating a state of the substrate from the transfer part or a processing part, and notifies the second control part that the transfer part is stopped due to the transfer error. The second control part retrieves image data of a predetermined period of time including the time that the transfer error occurs from the accumulation part, and converts the image data into a file.

12 Claims, 16 Drawing Sheets

(58) Field of Classification Search
CPC ............ H01L 21/67754; H01L 21/681; H01L
21/68764; H01L 21/68771; H01L
21/02164; H01L 21/02219; H01L
21/02274; H01L 21/0228; H01L
21/32051; H01L 21/67017; H01L
21/67069; H01L 21/67109; H01L
21/67126; H01L 21/6719; H01L
21/67207; H01L 21/67213; H01L
21/67265; H01L 21/67703; H01L
21/67739; H01L 21/6777; H01L 21/67288
See application file for complete search history.

(56) References Cited

U.S. PATENT DOCUMENTS

| | | | | |
|---|---|---|---|---|
| 2002/0132381 A1* | 9/2002 | Taira | ................... | G01R 31/2831 438/16 |
| 2002/0181757 A1* | 12/2002 | Takeuchi | ................. | G06T 7/001 382/149 |
| 2003/0058444 A1* | 3/2003 | Nara | ................... | G03F 7/70616 356/394 |
| 2004/0002016 A1* | 1/2004 | Rivers | ................. | H01L 51/0013 430/200 |
| 2004/0021856 A1* | 2/2004 | Nishiyama | ............. | G01N 21/94 356/237.2 |
| 2005/0016818 A1* | 1/2005 | Ito | ..................... | H01L 21/67259 198/345.1 |
| 2005/0105790 A1* | 5/2005 | Yasutomi | ............... | H01L 21/681 382/144 |
| 2007/0009345 A1* | 1/2007 | Hall | ................... | H01L 21/67775 414/222.01 |
| 2007/0085905 A1* | 4/2007 | Batson | .............. | H01L 21/67265 348/92 |
| 2007/0142952 A1 | 6/2007 | Yamamoto et al. | | |
| 2008/0094593 A1* | 4/2008 | Shibazaki | ............ | G03F 7/70725 355/53 |
| 2009/0114150 A1* | 5/2009 | Yoneda | ............. | H01L 21/67253 118/696 |
| 2009/0114346 A1* | 5/2009 | Yashima | ............ | G05B 19/4184 156/345.24 |
| 2009/0177413 A1* | 7/2009 | Nishiyama | .............. | G01N 21/94 702/35 |
| 2010/0152887 A1* | 6/2010 | Kawasaki | ............ | G05B 19/409 700/228 |
| 2011/0158774 A1* | 6/2011 | Yamaguchi | ........ | H01L 21/67265 414/222.02 |
| 2015/0293464 A1* | 10/2015 | Shibazaki | ............ | G03F 7/70725 355/72 |

FOREIGN PATENT DOCUMENTS

| | | |
|---|---|---|
| JP | 2005-116734 A | 4/2005 |
| JP | 2006-120820 A | 5/2006 |
| JP | 2007-173305 A | 7/2007 |
| JP | 2010-161346 A | 7/2010 |
| KR | 10-0435216 B | 6/2004 |

\* cited by examiner

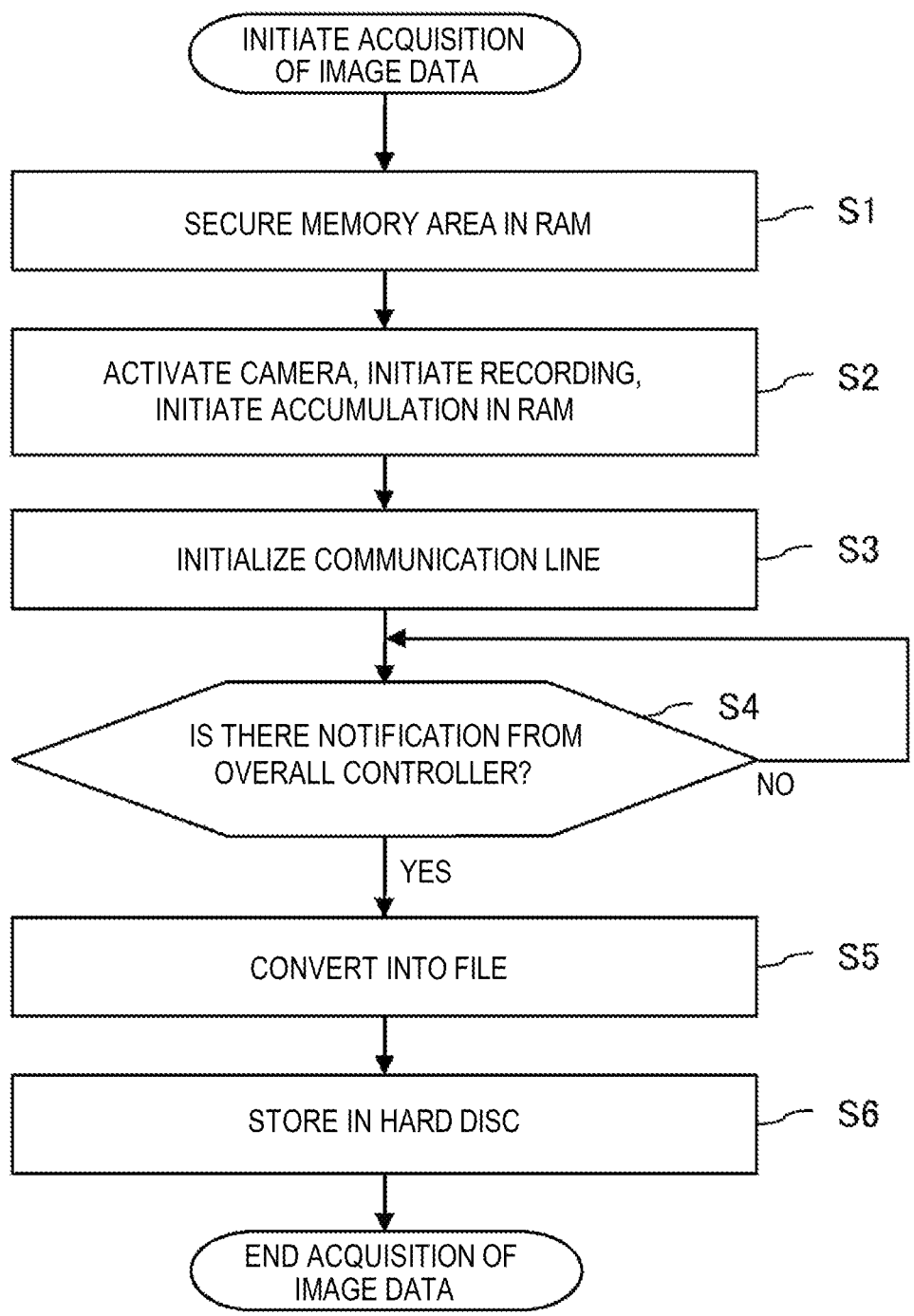

ND DEVICE

TECHNICAL FIELD

The present disclosure relates to a substrate processing apparatus equipped with a transfer part for transferring a substrate to a processing chamber.

BACKGROUND

A substrate processing apparatus is configured, for example, to transfer a substrate into a processing chamber using a transfer part and perform predetermined processing on the substrate in the processing chamber. In some cases, while a substrate is transferred, the substrate may be misaligned, dropped, or broken, for example, due to a problem of the transfer part or a pressure difference between the inside and the outside of the processing chamber. A detection part (e.g., a sensor such as an optical sensor, a mapping sensor, etc.) which functions to detect the existence of a substrate may detect a transfer error when a state of existence of a substrate at a predetermined position differs from an expected state. In this case, although the occurrence of the transfer error can be detected, a detailed state of the substrate (e.g., misalignment, drop, breakage, etc.) or a cause leading to the state may not be perceived immediately.

In order to solve the above problems, a recording part such as a video camera may be installed in the substrate processing apparatus for use in analyzing a transfer error. However, if image data are continuously stored in the substrate processing apparatus that operates all the time, since the data for the occurrence of a transfer error needs to be picked up from a large amount of the image data, a long time is needed to analyze the image data. Thus, this operation is inefficient because measures such as regularly erasing a memory medium by a maintenance operator are required.

SUMMARY

The present disclosure provides a substrate processing apparatus that is configured to record operations of transferring a substrate as image data, and to efficiently collect and store the image data for use in analyzing a transfer error.

According to one embodiment of the present disclosure, a substrate processing apparatus includes a transfer part configured to transfer a substrate; a processing part configured to process the substrate; a detection part configured to detect a transfer error occurring when the substrate is transferred by the transfer part; a first control part configured to, if the transfer error is detected by the detection part, stop the transfer part; a recording part configured to record transfer operation of the substrate by the transfer part as image data; and a second control part configured to accumulate the image data recorded by the recording part in an accumulation part, wherein the first control part is further configured to acquire information indicating a state of the substrate from the transfer part or the processing part and provides the second control part with a notification indicating that the transfer part is stopped in response to the transfer error, and wherein the second control part is further configured to read, from the accumulation part, the image data of a predetermined time interval including a time point when the transfer error occurs and converts the image data into a file.

According to another embodiment of the present disclosure, a substrate processing apparatus includes a transfer part configured to transfer a substrate; a processing part configured to process the substrate; a recording part configured to record a transfer operation of the substrate by the transfer part as image data; an operation part configured to operate display on a plurality of screens; and a control part configured to control the transfer part, the processing part, the recording part, and the operation part in association with information indicating a state of the substrate, wherein the control part is further configure to include a first storage part configured to store, among substrate processing result information including transfer history information of the substrate by the transfer part and production information indicating a substrate processing situation by the processing part, the transfer history information, and a second storage part configured to store the production information among the substrate processing result information, if a screen for displaying the transfer history information is selected, display the image data recorded by the recording part together with the transfer history information on the operation part, and if a screen for displaying the production information is selected, display the image data recorded by the recording part together with the production information on the operation part.

According to still another embodiment of the present disclosure, there is provided a substrate processing apparatus, including a transfer part configured to transfer a substrate; a detection part configured to detect a transfer error occurring when the substrate is transferred by the transfer part; a transfer control part configured to control transfer of the substrate by the transfer part; a recording part configured to record transfer operation of the substrate by the transfer part as image data; and a primary control part configured to convert the image data into a file, by dividing the image data recorded by the recording part based on a predetermined time period or a time period between predetermined events, and store the file in a memory part, wherein the primary control part is further configured to generate error information including an error notification indicating occurrence of the transfer error, time data indicating a time point when the transfer error occurs, a recipe content upon the occurrence of the transfer error, and monitoring data indicating a state of the substrate processing apparatus upon the occurrence of the transfer error, associate the file including the image data upon the occurrence of the transfer error with the error information while associating numerical data including a position and a velocity of the transfer part upon the occurrence of the transfer error with the error information, associate comparative data, obtained by comparing image data and numerical data in a normal state which are pre-stored in the memory part with the image data and the numerical data upon the occurrence of the transfer error to generate comparative data and extracting differences between the data, with the error information, and display the error information on an operation screen installed in the primary control part.

Effect of the Invention

According to some embodiments of the present disclosure, since image data concerning substrate transfer can be efficiently collected and stored for use in analyzing a transfer error by displaying image data and a substrate state upon the occurrence of the transfer error, the cause of the transfer error can be easily determined.

BRIEF DESCRIPTION OF THE DRAWINGS

FIG. 5 illustrates a flowchart of collecting and storing image data by the image controller according to the first embodiment of the present disclosure.

DETAILED DESCRIPTION

<First Embodiment of the Present Disclosure>

Hereinafter, a first embodiment of the present disclosure will be described.

(1) Configuration of Substrate Processing Apparatus

Figure 1:
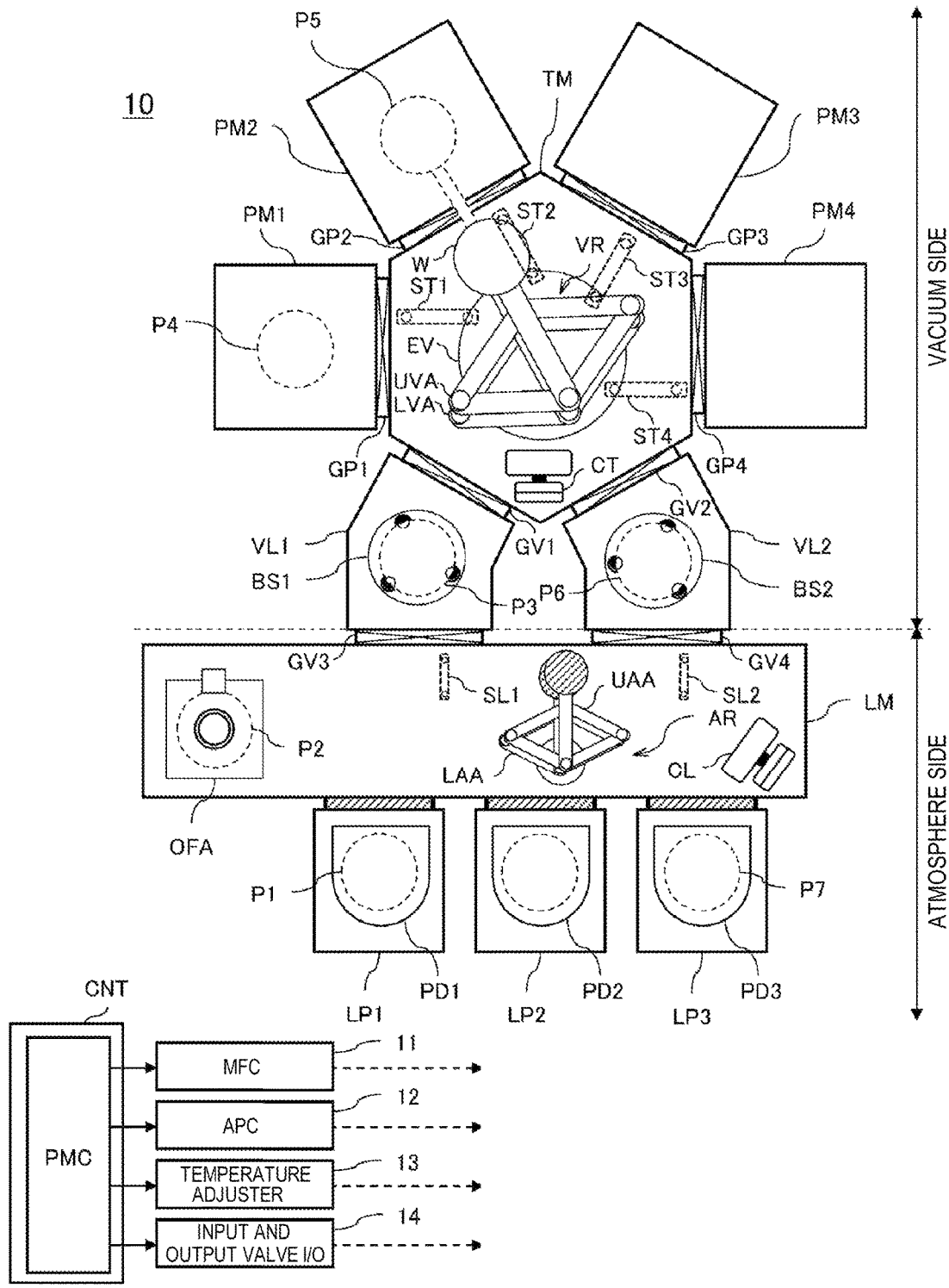
FIG. 1 schematically illustrates a configuration of a substrate processing apparatus according to a first embodiment of the present disclosure.

A configuration of a substrate processing apparatus according to the present embodiment will be described with reference to FIG. 1. FIG. 1 schematically illustrates the configuration of a single-wafer and cluster type substrate processing apparatus 10 according to the present embodiment.

As shown in FIG. 1, the substrate processing apparatus 10 is divided into a vacuum side and an atmosphere side.

(Configuration of Vacuum Side)

An airtight vacuum transfer chamber TM, vacuum load lock chambers VL1 and VL2 (e.g., auxiliary chambers), and process chambers PM1, PM2, PM3, and PM4 are installed in the vacuum side of the substrate processing apparatus 10. The vacuum load lock chambers VL1 and VL2 and the process chambers PM1 to PM4 are arranged in a star shape around the vacuum transfer chamber TM. In the description below, when any one of the plurality of components such as the process chambers PM1 to PM4 and the vacuum load lock chambers VL1 and VL2 is indicated, the reference numerals without numerical suffixes may be used (for example, "the process chamber PM").

The vacuum transfer chamber TM is configured with a load lock chamber structure that is capable of withstanding pressure below atmospheric pressure (e.g., negative pressure) such as a vacuum state. In this embodiment, a casing of the vacuum transfer chamber TM may be formed to have a hexagonal shape when viewed from a plane view and have a box shape with both lower and upper end portions closed.

A vacuum side robot VR as a first transfer part is installed within the vacuum transfer chamber TM. The vacuum side robot VR transfers a wafer W as a substrate, which is made of silicon (Si) or the like, between the vacuum load lock chambers VL1 and VL2 and the process chambers PM1 to PM4 while the wafer W is held on an upper arm UVA or a lower arm LVA that is a substrate mounting part. A wafer W may be transferred to a target chamber, for example, by replacement operation in which wafers W are approximately simultaneously loaded and unloaded. In addition, the vacuum side robot VR is configured to be lifted and lowered by an elevator EV while airtightness of the vacuum transfer chamber TM is maintained. Further, each of the upper arm UVA and the lower arm LVA is configured to stretch in a horizontal direction, and rotate and move in a horizontal plane.

In addition, wafer detection sensors ST1, ST2, ST3, and ST4 (whose PM1 to PM4 sides are shown), which are used as detection parts for detecting whether or not there is a wafer W, are installed at predetermined positions, respectively, in the vacuum transfer chamber TM and also in front of gate valves GV1, GV2, GP1, GP2, GP3, and GP4 (in the vicinity of positions through which a wafer W may pass when it is loaded into and unloaded from the vacuum load lock chambers VL1 and VL2 and the process chambers PM1 to PM4). As such, the wafer detection sensors ST1, ST2, ST3, and ST4 are configured to detect wafers W placed on the upper arm UVA and the lower arm LVA.

In addition, a camera CT is installed in the vacuum transfer chamber TM as a first recording part, such as a compact video camera or a web camera, for recording transfer operations by the vacuum side robot VR as image data, such as still or moving image data. In some embodiments, a plurality of the cameras CT may be installed. Specifically, they may be installed at a plurality of positions, where movement or transfer of a wafer W can be easily detected, such as front upper positions of the vacuum load lock chambers VL1 and VL2 and the process chambers PM1 to PM4. In addition, an inspection window (not shown) may be installed in a sidewall or the like of a predetermined process chamber PM and a camera may be installed at a position from which the inside of the process chamber PM can be viewed through the inspection window so that the transfer operation in the process chamber PM can be recorded. The above configuration is suitable when the camera cannot be installed inside the process chamber PM since processing is performed using a corrosive gas, plasma or the like, or under high temperature environments.

Accordingly, when a transfer error is detected by the wafer detection sensors ST1 to ST4 and the like, the analysis of a transfer error becomes easy.

When the state of a wafer W, which is different from an expected state, is detected by the wafer detection sensors and thus a transfer error occurs, a detailed state of the wafer W, such as misalignment, drop, or breakage, can be immediately perceived by confirming the image data. In addition, maladjustment of the arms UVA and LVA of the vacuum side robot VR, contaminants or wear of the arms UVA and LVA or substrate mounting parts installed at respective chambers, which will be described later, air current generated by a pressure difference between the respective chambers when the gate valves GV and GP are opened, and the like may be considered as the causes leading to the state of the wafer W such as misalignment, drop, or breakage. In this case, analysis using the image data, in addition to monitoring data, transfer trace data, error logging data, and the like indicating a transfer state of a substrate when the transfer error occurs, can specify the cause of the transfer error, reducing the time for analysis.

In this manner, in the present embodiment, the camera CT is installed within the vacuum transfer chamber TM or the like, and the image data recorded by the camera CT are used. Specifically, as will be described later, by displaying information indicating the detailed state of the wafer W (state information of the wafer W) and substrate transfer information from the image data on the same screen, it becomes easy to specify the cause of the transfer error, making it possible to analyze the transfer error in a short time.

Each of the process chambers PM1 to PM4 functions as a processing chamber giving a wafer W an added value, such as ashing, film formation (Chemical Vapor Deposition: CVD) using chemical reaction, or the like. In this case, any process chamber PM includes a substrate mounting part (not shown), which holds a wafer W, or a variety of components according to its functions, for example, gas introduction and exhaust, temperature control, and plasma discharge mechanisms. These mechanisms include a mass flow controller (MFC) 11 for controlling a flow rate of process gas supplied into the process chamber PM, an auto pressure controller (APC) 12 for controlling pressure in the process chamber PM, a temperature adjuster 13 for controlling temperature in the process chamber PM, an input and output valve I/O 14 to control whether a valve supplies or exhausts the process gas, and the like. The above-described respective components are electrically connected to a process chamber controller PMC provided in a control part CNT. The configuration of the control part CNT will be described later.

Mainly, processing parts according to the present embodiment are configured by the process chambers PM1 to PM4, each of which has the MFC 11, the APC 12, the temperature adjuster 13, the input and output valve I/O 14, and the like.

Each of the vacuum load lock chambers VL1 and VL2 functions as an auxiliary chamber for loading a wafer W into the vacuum transfer chamber TM or unloading a wafer W from the vacuum transfer chamber TM. Buffer stages BS1 and BS2, as substrate mounting parts for temporarily supporting a wafer W when the wafer W is loaded and unloaded, are located inside the vacuum load lock chambers VL1 and VL2, respectively. Each of the buffer stages BS1 and BS2 may be configured as slots of a multi-stage type for holding a plurality (for example, two sheets) of wafers W.

The vacuum load lock chambers VL1 and VL2 are in communication with the vacuum transfer chamber TM through the gate valves GV1 and GV2, respectively, and with an atmosphere transfer chamber LM, which will be described later, through gate valves GV3 and GV4, respectively. Thus, by opening the gate valves GV3 and GV4 and closing the gate valves GV1 and GV2, it is possible to transfer a wafer W between the vacuum load lock chambers VL1 and VL2 and the atmosphere transfer chamber LM while maintaining vacuum and airtightness within the vacuum transfer chamber TM.

In addition, the vacuum load lock chambers VL1 and VL2 are configured in a load lock chamber structure, which can withstand negative pressure below atmospheric pressure, such as a vacuum state, and the inside of each of the vacuum load lock chambers VL1 and VL2 may be vacuum-exhausted. Therefore, after the insides of the vacuum load lock chambers VL1 and VL2 are vacuum-exhausted with the gate valves GV3 and GV4 closed, a wafer W can be transferred between the vacuum load lock chambers VL1 and VL2 and the vacuum transfer chamber TM by opening the gate valves GV1 and GV2 while maintaining a vacuum state of the vacuum transfer chamber TM.

(Configuration of Atmosphere Side)

As described above, the atmosphere side of the substrate processing apparatus 10 includes the atmosphere transfer chamber LM connected to the vacuum load lock chambers VL1 and VL2 and load ports LP1 to LP3 as substrate accommodation parts for holding front opening unified pods (FOUPs) (hereinafter, referred to as pods PD1 to PD3) which are connected to the atmosphere transfer chamber LM and serve as substrate accommodating containers.

A clean air part (not shown) for supplying clean air to the inside of the atmosphere transfer chamber LM is installed in the atmosphere transfer chamber LM.

For example, an atmosphere side robot AR as a second transfer part may be installed in the atmosphere transfer chamber LM. The atmosphere side robot AR transfers a wafer W between the vacuum load lock chambers VL1 and VL2 and the load ports LP1 to LP3. The atmosphere side robot AR has an upper arm UAA and a lower arm LAA, which are substrate mounting parts in the same manner as described with respect to the vacuum side robot VR.

In addition, wafer detection sensors SL1 and SL2 as detection parts for detecting the existence of a wafer W are also installed at predetermined positions, respectively, in the atmosphere transfer chamber LM and in front of the gate valves GV3 and GV4 (in the vicinity of positions through which a wafer W may pass when it is loaded into and unloaded from the vacuum load lock chambers VL1 and VL2) and configured to detect wafers W held on the upper arm UAA and the lower arm LAA.

In addition, a camera CL is located in the atmosphere transfer chamber LM as a second recording part, such as a compact video camera or a web camera, to record transfer operations by the atmosphere side robot AR as image data, such as a still or moving image data. In some embodiments, a plurality of the cameras CL may be installed. Specifically, they may be installed at a plurality of positions, where movement or transfer of a wafer W can be easily detected, such as front upper positions of the vacuum load lock chambers VL1 and VL2.

Accordingly, when a transfer error is detected by the wafer detection sensors SL1 and SL2, the analysis of the transfer error becomes easy.

In a related art, although occurrence of a transfer error can be perceived by the wafer detection sensors, the cause of the transfer error and the like are specified by analyzing the data accumulated in the substrate processing apparatus, such as monitoring data, transfer trace data, error logging data, and the like indicating a state of the substrate processing apparatus, and estimating the occurrence cause. Since such analysis of a transfer error takes a long time, it is difficult to specify the occurrence cause of the transfer error.

However, in the present embodiment, using the image data recorded by the camera CL, by displaying the detailed state information on a wafer W and the substrate transfer information from the image data on the same screen, it becomes easy to specify the cause of a transfer error, making it possible to analyze the transfer error in a short time.

In addition, an orientation flat aligner OFA that positions the crystal orientation in a wafer W or the like is installed as a substrate position correction device in the atmosphere transfer chamber LM. When a wafer W is a notch type, a notch aligner may be installed as the substrate position correction device.

The load ports LP1 to LP3 are configured to mount the pods PD1 to PD3, respectively, which are substrate accommodating containers for accommodating a plurality of wafers W. A plurality of slots (not shown) as accommodation parts that accommodates wafers W, respectively, is installed in the pods PD1 to PD3. The load ports LP1 to LP3 are configured to read or write IDs (carrier IDs) identifying the pods PD1 to PD3 if the pods PD1 to PD3 are mounted, respectively.

In addition, the load ports LP1 to LP3 are configured to perform mapping of confirming whether or not a wafer W is placed in each slot of the pods PD1 to PD3 when the pods PD1 to PD3 are mounted, and when the substrate processing is terminated and all wafers W are then unloaded. Accordingly, a slot position in which a wafer W is accommodated is identified and abnormalities, such as whether the wafer W is properly accommodated in each slot position, whether the slot position for the wafer W is changed before and after the substrate processing, etc., are determined. Examples in which a wafer W is not properly accommodated in its slot position may include a case in which a wafer W is obliquely accommodated over a slot (i.e., "cross"), a case in which a wafer W on an upper slot falls down and thus two or more wafers are accommodated in a single slot (i.e., "double"), or the like, due to defect, crack, or misalignment of the wafer W.

In a related art, when such abnormalities occur, a large amount of time and labor are needed to specify the cause. However, in the present embodiment, it is possible to save time or labor for specifying the cause by displaying information on the above-described image data and the detailed state information of a wafer W on the same screen to analyze an abnormality in a slot position.

Hereinabove, although the substrate processing apparatus 10 of the present embodiment is described, the number or configuration of the respective chambers or the combination thereof are not limited to the foregoing but may be appropriately selected.

Figure 2:
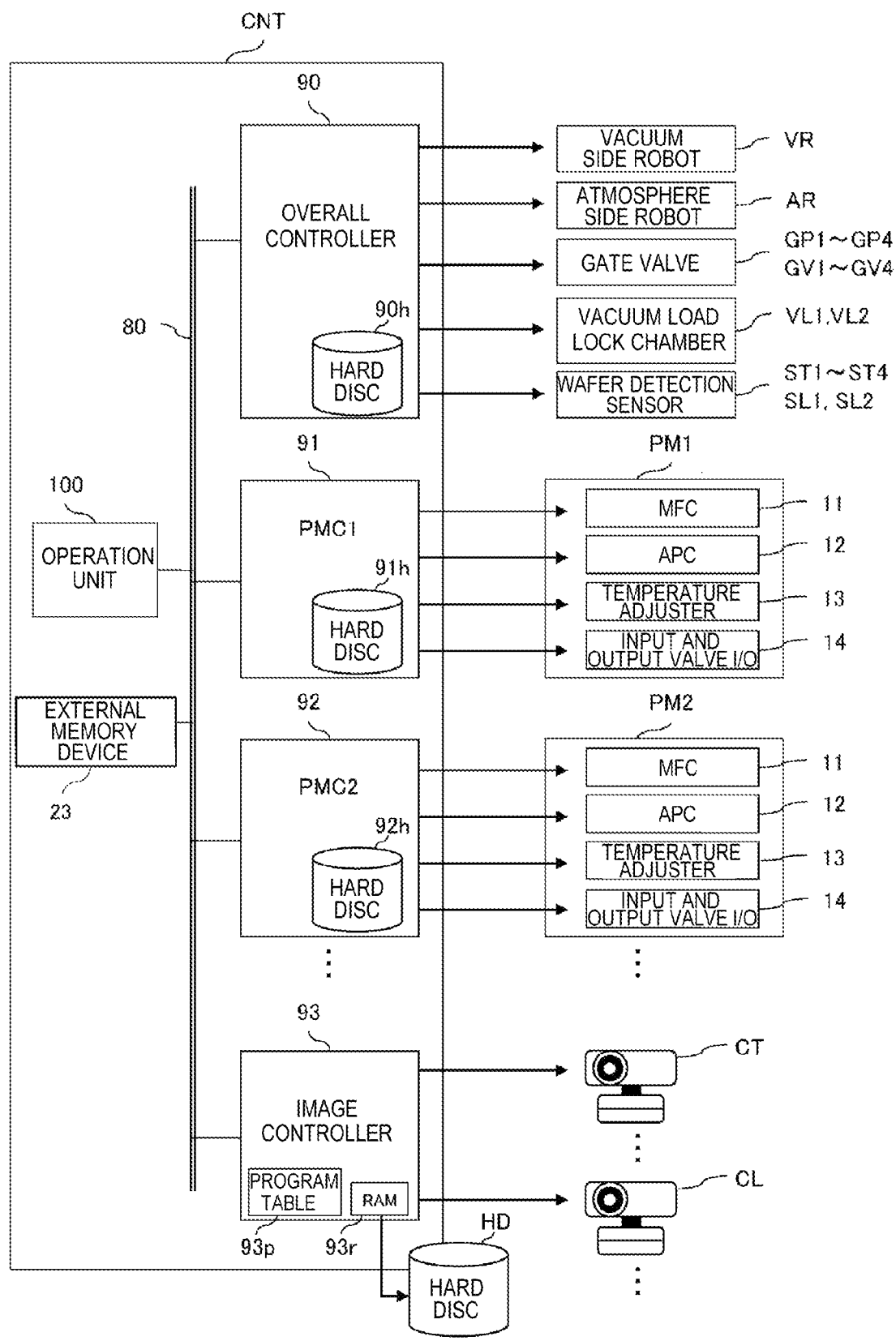
FIG. 2 shows a block diagram of a configuration of a control part in the substrate processing apparatus according to the first embodiment of the present disclosure.

(2) Configuration of Control Part Each component of the substrate processing apparatus 10 is controlled by the control part CNT. An example of the configuration of the control part CNT is shown in FIG. 2. The control part CNT includes an overall controller 90 as a first control part, process chamber controllers, i.e., PMC1 91, PMC2 92, . . . , an image controller 93 as a second control part, and an operation part 100 that receives manipulation of an operator, which are connected to one another so as to allow data to be mutually exchanged through a LAN line 80. In addition, instead of the LAN line 80, a USB line, a digital I/O line, or the like may be used.

(Overall Controller)

The overall controller 90 is connected to each of the vacuum side robot VR, the atmosphere side robot AR, the gate valves GP1 to GP4 and GV1 to GV4, and the vacuum load lock chambers VL1 and VL2. The overall controller 90 is configured to control operations of the vacuum side robot VR and the atmosphere side robot AR, opening/closing operations of the gate valves GP1 to GP4 and GV1 to GV4, and exhausting operations of the interiors of the vacuum load lock chambers VL1 and VL2. The overall controller 90 is also configured to acquire state information indicating a detailed state of a wafer W from the respective components constituting the transfer parts or the processing parts.

In addition, the overall controller 90 is connected to each of the wafer detection sensors ST1 to ST4, SL1, SL2, and the like as the above-described detection parts, and prepares and frequently updates position information indicating a position of a wafer W in the substrate processing apparatus 10 based on the detection signals from the wafer detection sensors ST1 to ST4, SL1, SL2, and the like. The overall controller 90 also control operations of the vacuum side robot VR as the first transfer part, the atmosphere side robot AR as the second transfer part, the gate valves GP1 to GP4 and GV1 to GV4, or the like, based on data such as process processing situations of a wafer W, a wafer ID or carrier IDs for identifying the wafer W or the pods PD1 to PD3, a recipe performed on the wafer W, and the like, in addition to the position information of the wafer W and accommodation information designating which slot in the pods PD1 to PD3 accommodates the wafer W.

Also, when a transfer error is detected by the wafer detection sensors ST1 to ST4, SL1, SL2, and the like, the overall controller 90 stops the transfer operation by the vacuum side robot VR or the atmosphere side robot AR and provides the image controller 93 with a notification indicating the stopping.

In addition, the overall controller 90 is provided with a hard disc 90h as a first storage part. The hard disc 90h is configured such that various pieces of information on the transfer are stored therein by the overall controller 90. Also, the hard disc 90h readably stores a control program and the like for controlling the operation of the substrate processing apparatus 10 through the overall controller 90.

(Process Chamber Controller)

Each of the process chamber controllers PMC1, PMC2, . . . is connected to the MFC 11, the APC 12, the temperature adjuster 13, the input and output valve I/O 14 and the like installed in the process chamber PM1, PM2, . . . . In addition, each of the process chamber controllers PMC1, PMC2, . . . is configured to control operations of the gas introduction and exhaust mechanisms, the temperature control and plasma discharge mechanisms, and the like of the process chamber PM1, PM2, . . . .

In addition, hard discs 91h, 92h, . . . as second storage parts are installed in the process chamber controllers PMC1, PMC2, . . . , respectively. The hard discs 91h, 92h, . . . are configured such that various pieces of information on the substrate processing are stored therein by the process chamber controllers PMC1, PMC2, . . . , respectively. In addition, the hard discs 91h, 92h, . . . readably store control programs and the like for controlling the operation of the substrate processing apparatus 10 through the process chamber controllers PMC1, PMC2, . . . , respectively.

(Image Controller)

The image controller 93 is connected to the cameras CT, the cameras CL, and the like as the recording parts, which are installed within the vacuum transfer chamber TM, the atmosphere transfer chamber LM, and the like, through a USB line, a LAN line or the like. In addition, the image controller 93 is provided with a RAM 93r as an accumulation part for accumulating the image data recorded by the cameras CT and CL and the like, and a program table 93p in which an accumulation condition of the image data in the RAM 93*r* or the like is defined. The program table 93*p* is readably stored in a memory device (not shown) or the like, for example, which is installed in the image controller 93. In addition, a hard disc HD as a memory part is connected to the image controller 93. The memory device or hard disc HD readably stores a control program and the like for controlling the operations of the cameras CT, the cameras CL, and the like through the image controller 93.

If the image controller 93 is activated, the image controller 93 reads the program table 93*p*, secures a necessary portion in the memory area of the RAM 93*r* to have the image data accumulated therein according to the accumulation condition and the like, and initiates recording of the image data by activating predetermined cameras CT and CL and the like. In addition, the image controller 93 initiates the accumulation of the image data for a predetermined accumulation time interval in the RAM 93*r* at a predetermined period of time according to the accumulation condition and the like. Also, the image controller 93 waits for a notification from the overall controller 90 after the communication is established by initiating the communication line with the overall controller 90.

After installing an operation screen or the like at the image controller 93, the image data recorded by the respective cameras CT and CL and the like may be appropriately displayed as the substrate transfer information on the operation screen. Alternatively, the image data may be displayed on an operation screen (not shown) installed in the operation part 100. Here, it may be displayed on the operation screen that the image data can be stored when a transfer error occurs.

In addition, if the image controller 93 receives, from the overall controller 90, the notification indicating that the vacuum side robot VR or the atmosphere side robot AR is stopped because of a transfer error, the image controller 93 terminates the accumulation of the image data, reads, from the RAM 93*r*, the image data for a predetermined time interval including a time point when the transfer error occurred, converts the image data into a file, and stores the file in the hard disc HD. Once the data is stored in the hard disc HD, the image controller 93 reactivates the accumulation of the image data.

According to the present embodiment, the image data before and after a transfer error occurs are stored in the hard disc HD in the manner as described above. Accordingly, for example, contrary to a case in which the image data are introduced and stored all the time, an effort to pick up a portion that is necessary for analyzing a transfer error from large amounts of image data is saved, making it possible to reduce the time necessary for the analysis. In addition, the continuous storing of image data in the substrate processing apparatus that operates all the time has a limitation due to a capacity limit of a memory medium. However, according to the present embodiment, a memory size of the hard disc HD may be small, and also, a load of the hard disc HD can be reduced.

Further, if the hard disc HD is configured, for example, as an external memory part, the file stored in the hard disc HD may be displayed on not only the operation screen of the image controller 93 or the operation part 100 but also, for example, a computer in an office area remote from a clean room in which the substrate processing apparatus 10 is installed. Accordingly, since it is easy to display or refer to the image data, the analysis of a transfer error becomes easier.

(Program Table)

Figure 3A:
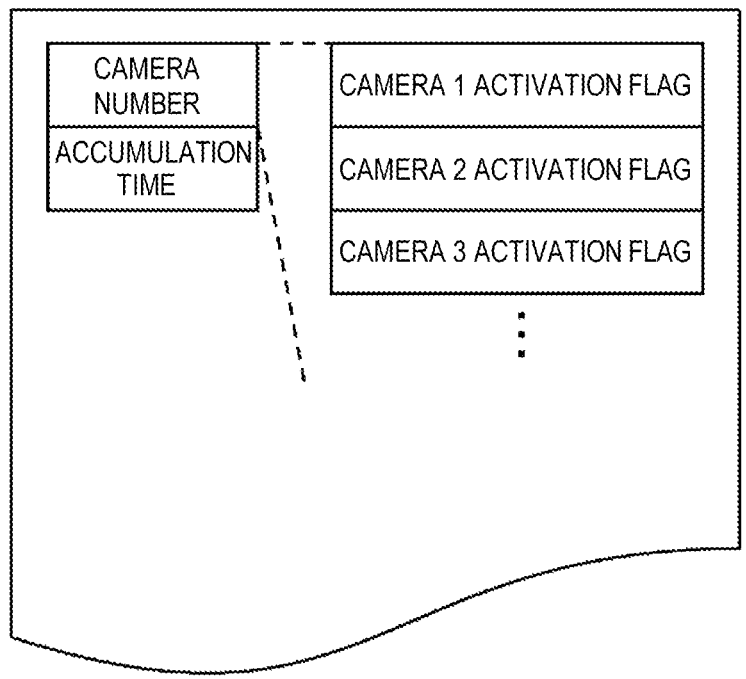
FIGS. 3A and 3B show examples of setting a program table provided in an image controller according to the first embodiment of the present disclosure.
Figure 3B:
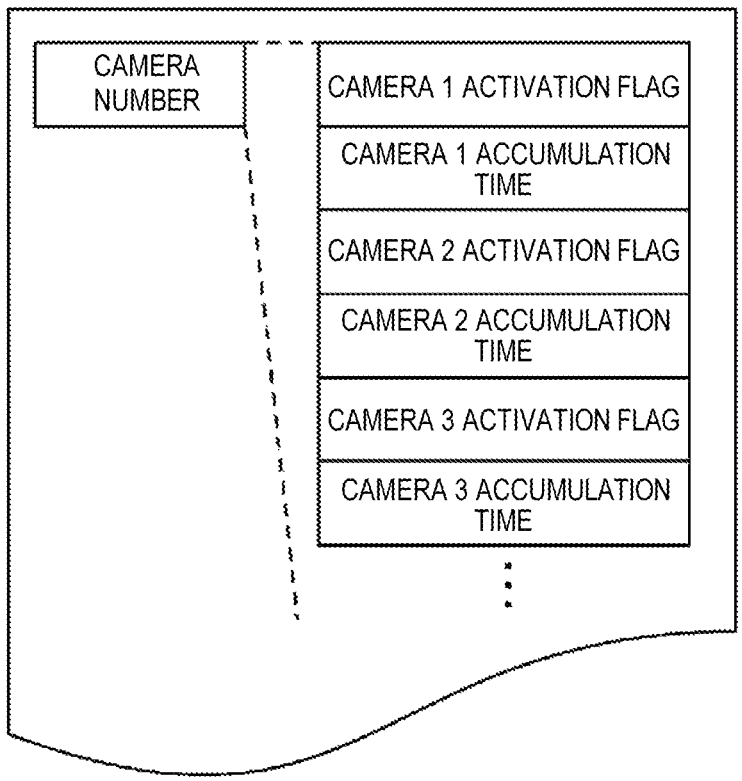

The accumulation conditions, such as the number of the cameras CT and CL and the like, whether or not they need to be activated, a period of time for accumulating image data in the RAM 93*r*, an accumulation time, and the like, are defined in the program table 93*p* provided to the image controller 93. FIGS. 3A and 3B show several examples of setting the accumulation conditions by the program table 93*p*. The program table 93*p* shown in FIG. 3A is configured to set whether or not activation of each camera is needed. In addition, the accumulation time of image data in the RAM 93*r* is generally set for all the cameras. On the other hand, like the program table 93*p* shown in FIG. 3B, the accumulation time of image data in the RAM 93*r* may also be set for each camera.

Here, predetermined events generated in the substrate processing apparatus 10 may be set as triggers for the period of time for accumulating image data in the RAM 93*r*. A specific example of an event that is an initial or end point of the period of time includes a timing at which the pod PD is mounted on the load port LP, a timing at which the vacuum side robot VR or the atmosphere side robot AR is moved to a predetermined position, a timing at which the gate valves GP and GV are opened or closed, and the like.

In addition, the accumulation time of image data in the RAM 93*r* may be set, for example, based on the time required for a predetermined operation by the transfer part such as the vacuum side robot VR or the atmosphere side robot AR. In this case, a time interval divided for each operation of approximately one minute may be set as the accumulation time, but it is preferred in some embodiments to set a time interval divided for an overall series of operations such as a time required for loading a wafer W into a predetermined process chamber PM, a time required for unloading a processed wafer W from the process chamber PM, and the like. In addition, if the processing time of a wafer W in the process chamber PM is also included in the accumulation time, analysis of a transfer error becomes easier even if misalignment, drop, or breakage of the wafer W occurs in the process chamber PM. In such a case, the accumulation time is set by adding the time required for processing a substrate. Thus, the accumulation time is the sum of the time required for loading a predetermined wafer W into the process chamber PM, a time for processing the predetermined wafer W in the process chamber PM, and a time required for unloading the predetermined wafer W from the process chamber PM. In addition, according to installation positions of the cameras CT and CL in the vacuum transfer chamber TM and the atmosphere transfer chamber LM, the time interval from a time point when a wafer W is loaded into the vacuum transfer chamber TM or the atmosphere transfer chamber LM to a time point when the wafer W is unloaded therefrom or the like may be set as the accumulation time.

As described above, when a transfer error occurs, the image data of the set accumulation time as a single part is converted into a file and the file is stored in the hard disc HD. Therefore, the image data for a predetermined time interval included in this file are image data acquired from the initial point to the end point of the accumulation time, or from the initial point of the accumulation time to a time point when a transfer error occurs and thus the accumulation is stopped.

In addition, the program table 93*p* is combined such that a predetermined sequence in automatic transfer processing of the substrate processing apparatus 10, which will be described later, is executed on the image controller 93 and predetermined results can be obtained, and functions as a program. Hereinafter, this program table 93p, the above-described control program, and the like are collectively referred to simply as a program. Also, the term "program" used herein may include a case in which the program includes solely the program table 93p, a case in which the program includes solely the control program, or a case in which the program includes both of them.

(Memory Area of RAM)

Figure 4A:
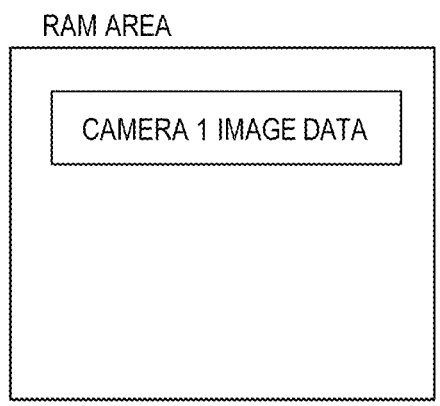
FIGS. 4A and 4B show examples of managing a memory area in a RAM secured by the image controller according to the first embodiment of the present disclosure.
Figure 4B:
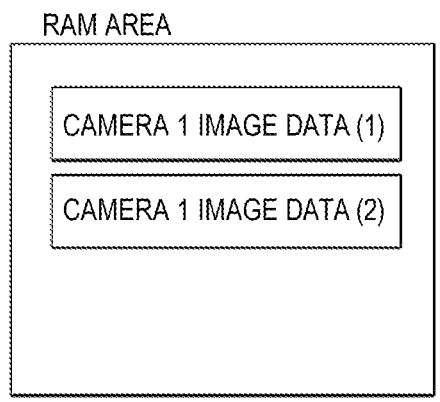

As described above, the image controller 93 secures a memory area in the RAM 93r according to the accumulation condition. FIGS. 4A and 4B show several examples of managing a memory area of the RAM 93r secured by the image controller 93. In the example of FIG. 4A, a memory area of an amount for the accumulation time defined by the accumulation condition is secured for the image data obtained from one camera. Therefore, an overwriting operation is performed from the head of the memory area whenever the period of time in the accumulation condition comes. On the other hand, as shown in FIG. 4B, a plurality of memory areas of an amount for a plurality of the accumulation times is secured for the image data from one camera. In this case, the image data are accumulated in the plurality of memory areas in sequence and if all the memory areas are full, an overwriting operation is performed from the initial memory area in sequence.

Hereinabove, in the present embodiment, if a transfer error occurs while the image data are overwritten on a predetermined memory area in the RAM 93r, the image data before and after the occurrence of the transfer error are stored in the hard disc HD. In this manner, since efficiencies of collecting and storing image data are improved, the image data can be acquired without overloading the RAM 93r or the hard disc HD, making it possible to analyze a transfer error in a short time.

(Operation Part)

The operation part 100 serves functions of providing system control commands and displaying on the operation screen. In addition, the operation part 100 serves functions of analyzing the substrate transfer information from the above-described image data, the detailed state information of a wafer W such as monitoring data and various logging data indicating a state of the substrate processing apparatus 10, and an alarm, and screen display and input reception such as editing a recipe or a parameter. Specifically, the operation part 100 is configured to display the substrate transfer information from image data and the detailed state information of a wafer W on the same screen.

Hereinabove, although the overall controller 90 and the image controller 93 are configured to be separate in the control part CNT, the overall controller 90 may incorporate the functions of the image controller 93 if performance or hardware requirements of the overall controller 90 are sufficient. In such a case, for example, the overall controller 90 may be provided with an overall control program and an image control program, and various data may be communicated between both the programs.

In addition, the control part CNT, or the overall controller 90, the image controller 93 and the like constituting the control part CNT are not limited to a case in which they are configured as a dedicated computer, and may be configured as a general-purpose computer having a central processing unit (CPU), a random access memory (RAM), a memory device, and I/O ports. For example, the control part CNT and the like according to the present embodiment may be implemented by preparing an external memory device 23 (for example, a magnetic tape, a magnetic disc such as a flexible disc or hard disc, an optical disc such as a CD or DVD, a magneto-optical disc such as an MO, or a semiconductor memory such as a USB memory or memory card) for storing the above-described programs, installing the programs on the general-purpose computer using the external memory device 23, and the like. In this case, the control part CNT, or the overall controller 90, the image controller 93 and the like constituting the control part CNT may be configured as separate computers, respectively, or some of them may be integrated in a single computer. In addition, a part for supplying a program to a computer is not limited to a case in which the supply is performed through the external memory device 23. For example, the programs may be supplied not through the external memory device 23 but using a communication part such as the internet or a dedicated line. In addition, the hard disc 90h provided in the overall controller 90, the memory device provided in the image controller 93, the external memory device 23 or the like includes a computer-readable recording medium. Hereinafter, they are collectively referred to simply as a recording medium. In addition, the term "recording medium" used herein may include a case in which the recording medium includes solely the hard disc 90h, a case in which the recording medium includes solely the memory device, a case in which the recording medium includes solely the external memory device 23, or a case in which the recording medium includes any combination thereof. In addition, the above-described hard disc 90h or the like may be configured as not only a hard disk drive (HDD) as described above, but also, for example, a flash memory or the like.

(3) Operation of Substrate Processing Apparatus

The automatic transfer processing performed by the above-described substrate processing apparatus 10 will be described with reference to FIGS. 1 and 5. FIG. 5 illustrates a flowchart of collecting and storing image data by the image controller 93. Also, in the following description, operations of the respective components in the substrate processing apparatus 10 are controlled by the control part CNT. The operations and controls are performed as one of the semiconductor device manufacturing processes, while some others are performed as one of the data analysis processes of a transfer error.

In addition, hereinafter, the term "unprocessed wafer W" refers to a wafer W that is not yet loaded into the substrate processing apparatus 10 from the load port LP, or a wafer W that is not processed in the process chamber PM into which the wafer W is to be loaded, among the wafers W loaded into the substrate processing apparatus 10 from the load port LP. Also, hereinafter, the term "processed wafer W" refers to a wafer W on which the entire processing is completed in the substrate processing apparatus 10, or a wafer W on which predetermined processing is completed in a predetermined process chamber PM.

(Activation of Image Controller)

As shown in FIG. 5, if the image controller 93 is activated, for example, by providing electric power to the substrate processing apparatus 10 or the control part CNT, the image controller 93 reads the program table 93p and secures a memory area in the RAM 93r according to the accumulation condition (S1). In addition, a predetermined camera CT or CL is activated according to the accumulation condition to initiate recording of image data and to initiate accumulating of the image data for a predetermined accumulation time interval in the RAM 93r at a predetermined period of time (S2). Also, the LAN line 80 is initiated to establish the communication with the overall controller 90 (S3). Thereafter, the process proceeds to wait for the notification from the overall controller 90 indicating that the transfer part is stopped (S4).

In addition, the gate valves GV1 and GV2 are closed and the gate valves GV3 and GV4 are opened so that the vacuum transfer chamber TM and the process chambers PM1 to PM4 are vacuum-exhausted. Also, the atmosphere transfer chamber LM is supplied with clean air so that the interior of the atmosphere transfer chamber LM is almost at atmospheric pressure.

(Transfer into Atmosphere Transfer Chamber)

When the above-described components are ready, for example, if the pod PD1 accommodating a plurality of unprocessed wafers W is mounted on the load port LP1, as shown in FIG. 1, a wafer W accommodated in a substrate position P1 in the pod PD1 is transferred to the atmosphere transfer chamber LM by the atmosphere side robot AR so that the wafer W is placed at a substrate position P2 on the orientation flat aligner (OFA) and subjected to the alignment of crystal orientation or the like.

(Transfer into Vacuum Load Lock Chamber)

Subsequently, the wafer W placed at the substrate position P2 is picked up by the atmosphere side robot AR and is transferred into, for example, the vacuum load lock chamber VL1, in a state where at least the gate valve GV3 is open, to be placed at a substrate position P3 on the buffer stage BS1. Then, the gate valve GV3 is closed and the vacuum load lock chamber VL1 is vacuum-exhausted.

(Transfer into Process Chamber)

If a pressure in the vacuum load lock chamber VL1 is reduced to a predetermined pressure, the gate valve GV 1 is opened with the gate valves GV3 and GV4 closed. Then, the wafer W placed at the substrate position P3 is picked up by the vacuum side robot VR and, for example, the gate valve GP1 is opened so that the wafer W is transferred into the process chamber PM1 and placed at a substrate position P4. Thereafter, the wafer W is subjected to predetermined processing by supplying the process chamber PM1 with process gas or heating the wafer W.

If the processing on the wafer W in the process chamber PM1 is completed, the processed wafer W placed at the substrate position P4 is picked up by the vacuum side robot VR and, for example, the gate valve GP2 is opened so that the wafer W is transferred into the process chamber PM2 and arranged at a substrate position P5. The wafer W in the process chamber PM2 is also subjected to a predetermined process by supplying process gas or heating the wafer W. In this manner, until the entire predetermined processing is performed on the wafer W, the transfer operations from and into predetermined process chambers PM may be successively performed. In this case, the number of the process chambers used or the transfer sequence is appropriately selected according to the scheduled processing.

(Transfer into Vacuum Load Lock Chamber)

If the entire necessary processing is completed, the processed wafer W placed at the substrate position P5 in the predetermined process chamber PM, for example, in the process chamber PM2, is picked up by the vacuum side robot VR and, for example, the gate valve GV2 is opened so that the wafer W is transferred into the vacuum load lock chamber VL2 and arranged at a substrate position P6 on the buffer stage BS2. Thereafter, the gate valve GV2 is closed, the interior of the vacuum load lock chamber VL2 is returned to an almost atmospheric pressure state by supplying the vacuum load lock chamber VL2 with clean gas, and the gate valve GV4 is opened.

(Accommodation in Pod Held on Load Port)

Subsequently, the processed wafer W placed at the substrate position P6 is picked up by the atmosphere side robot AR and transferred, for example, to the pod PD3 held on the load port LP3 to be accommodated in a substrate position P7 that is an empty slot.

In this manner, if the vacuum side robot VR or the atmosphere side robot AR performs predetermined transfer operations and a transfer error is not detected by the wafer detection sensors ST1 to ST4, SL1, SL2, and the like, then, the above-described processes are repeated until the automatic transfer processing is performed on all the unprocessed wafers W, while the transfer operations are recorded and accumulated. Thereafter, the pod PD3 accommodating the processed wafers W is unloaded from the load port LP3 to complete the automatic transfer processing.

(Operation in Occurrence of Transfer Error)

On the other hand, if a transfer error is detected by the wafer detection sensors ST1 to ST4, SL1, SL2, and the like, the overall controller 90 stops the transfer part such as the vacuum side robot VR and the atmosphere side robot AR. In addition, the overall controller 90 acquires state information of the wafer W from the respective components constituting the transfer parts or the processing parts. The overall controller 90 also provides the image controller 93 with the notification indicating that the transfer part is stopped. The overall controller 90 may acquire the state information on the wafer W during the automatic transfer processing, frequently, or appropriately.

As shown in FIG. 5, if the overall controller 90 provides the notification (S4→"YES"), the image controller 93 reads, from the RAM 93$r$, the image data of a predetermined time interval including a time point when the transfer error occurred and converts the image data into a file (S5). The converted file is stored in the hard disc HD (S6). Accordingly, the operation of collecting and storing the image data by the image controller 93 is terminated.

The substrate transfer information from the image data acquired in the manner as above is displayed along with the detailed state information of the wafer W on the same operation screen installed in the operation part 100 by manipulation of an operator or at a predetermined timing.

(4) Operation of Transfer Part

Transfer of a wafer W in the vacuum transfer chamber TM by the transfer part will be described in more detail with reference to FIG. 6.

FIG. 6A to 6F show operations of the vacuum side robot VR of the substrate processing apparatus 10. In this case, a processed wafer W (hereinafter, denoted as $W_2$) in a state waiting for unloading is in the process chamber PM (not shown) where wafers W are to be loaded and unloaded and the upper arm UVA and the lower arm LVA installed in the vacuum side robot VR replaces the processed wafer $W_2$ with an unprocessed wafer W (hereinafter, denoted as $W_1$). In addition, at least in the period of time for this transfer, the transfer operation by the vacuum side robot VR is recorded as image data by the camera CT installed in the vacuum transfer chamber TM.

Figure 6A:
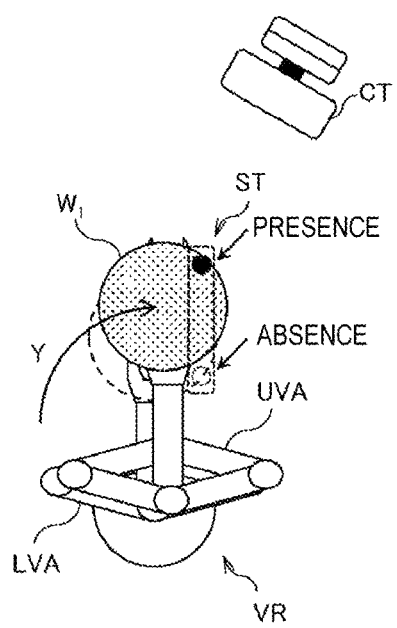
FIGS. 6A to 6F show operations of a vacuum side robot in the substrate processing apparatus according to the first embodiment of the present disclosure.

First, the unprocessed wafer $W_1$ is picked up, for example, from the inside of the vacuum load lock chamber VL (not shown) by the upper arm UVA and directed toward the process chamber PM (upward in the paper plane) by rotating the upper arm UVA in the Y-axis direction, as shown in FIG. 6A. Accordingly, the wafer $W_1$ on the upper arm UVA comes to a detection position of the wafer detection sensor ST in front of the process chamber PM. If the wafer $W_1$ is not misaligned or the like, "Wafer Presence" is determined by the wafer detection sensor ST. On the other hand, since the lower arm LVA holds no wafer, "Wafer Absence" is determined by the wafer detection sensor ST.

Figure 6B:
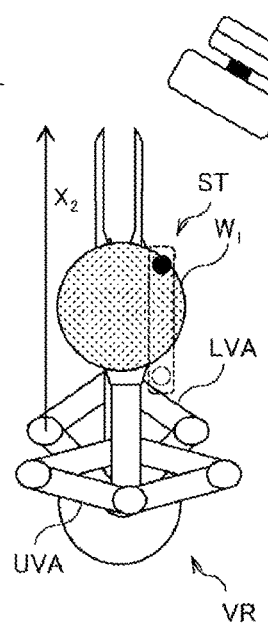
Figure 6C:
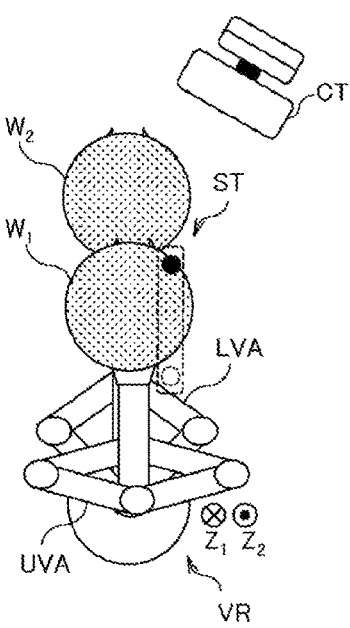

Next, the lower arm LVA is extended in the forward direction of an $X_2$ axis (i.e., toward the process chamber PM) as shown in FIG. 6B and lifted and lowered in the directions of $Z_1$ and $Z_2$ axes (in the direction vertical to the paper plane) to adjust its level to pick up the processed wafer $W_2$ in the process chamber PM as shown in FIG. 6C.

Figure 6D:
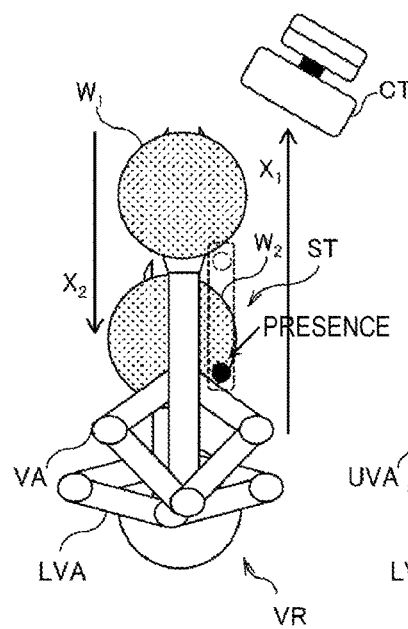

Subsequently, as shown in FIG. 6D, if the lower arm LVA with the wafer $W_2$ held is retracted in the backward direction of the $X_2$ axis (i.e., in the direction opposite to the process chamber PM), the wafer $W_2$ comes to the detection position of the wafer detection sensor ST. The wafer $W_2$ is detected as "Wafer Presence" by the wafer detection sensor ST.

Figure 6E:
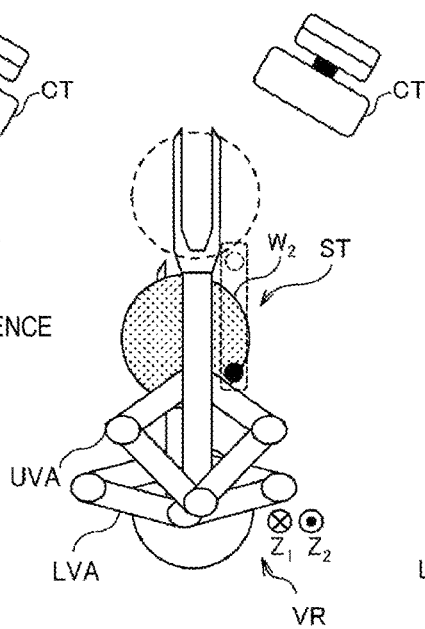

On the other hand, the upper arm UVA with the unprocessed wafer $W_1$ held extends in the forward direction of the $X_1$ axis following the retracting operation of the lower arm LVA and lifted and lowered in the directions of the $Z_1$ and $Z_2$ axes, as shown in FIG. 6E, so that the wafer $W_1$ is moved and mounted in the process chamber PM.

Figure 6F:
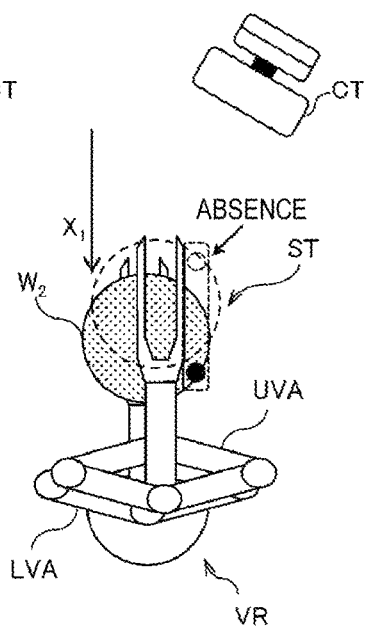

Subsequently, as shown in FIG. 6F, if the upper arm UVA that has moved and mounted the wafer $W_1$ to the process chamber PM is retracted in the backward direction of the $X_1$ axis, the upper arm UVA comes to the detection position of the wafer detection sensor ST and "Wafer Absence" is determined by the wafer detection sensor ST since the upper arm UVA holds no wafer. Accordingly, the replacement operation of the wafers $W_1$ and $W_2$ with respect to the process chamber PM is completed.

In this manner, if the presence or absence of a wafer W, which is determined in response to various operations of the upper arm UVA and the lower arm LVA, is proper for an expected state, the wafer detection sensor ST does not detect a transfer error.

On the other hand, when misalignment, drop, breakage, or the like of the wafer W causes a problem to the transfer of the wafer W and thus the wafer W that is expected not to exist is detected or the wafer W that is expected to exist is not detected, a transfer error is detected by the wafer detection sensor ST and thus the transfer operation is stopped.

The conversion into a file and the storage of the file in the hard disc HD upon the occurrence of a transfer error will be described with reference to a specific example shown in FIG. 7.

Figure 7:
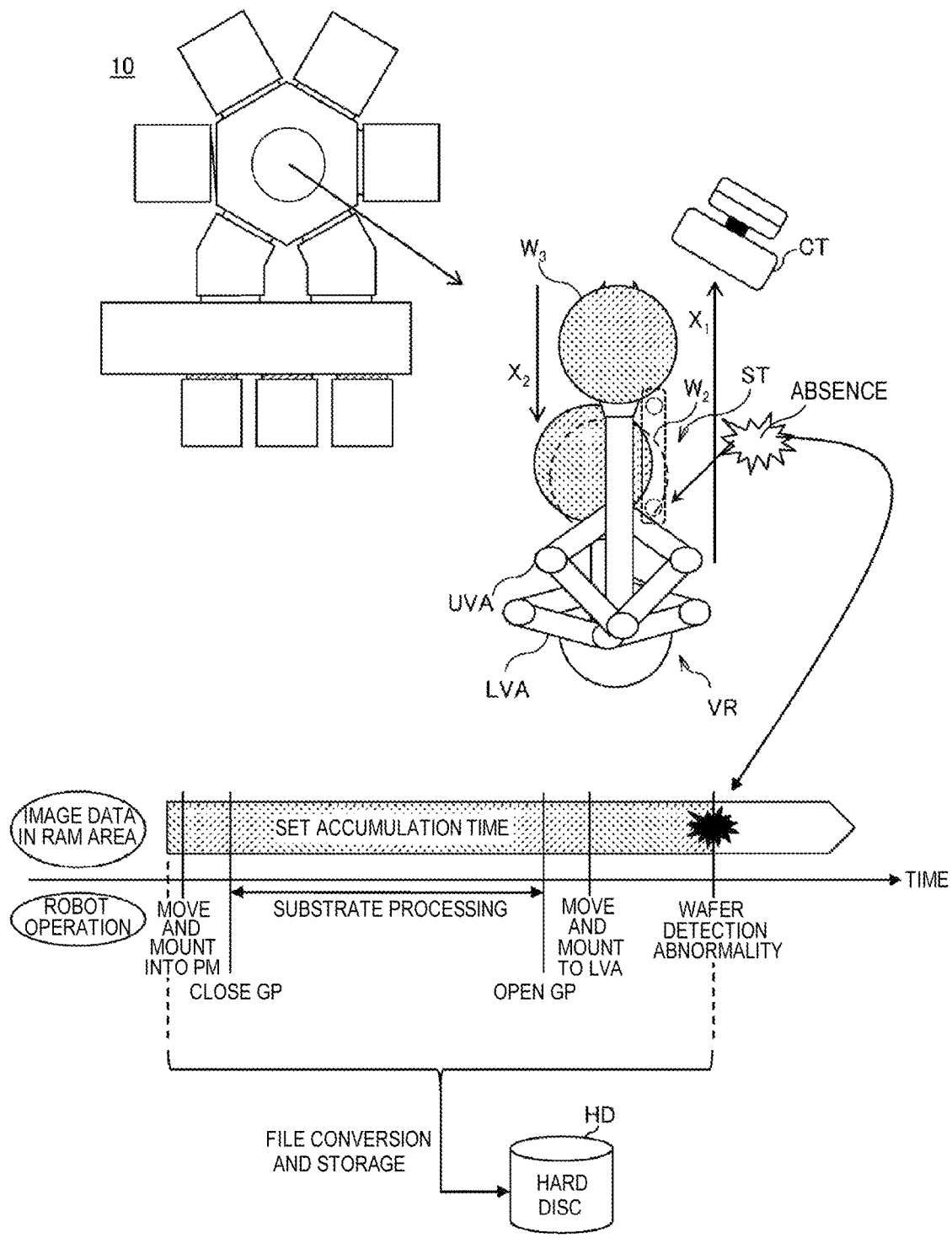
FIG. 7 shows an overview diagram of converting image data into a file and storing the file in a hard disc by the image controller according to the first embodiment of the present disclosure.

FIG. 7 shows an overview diagram of converting image data into a file and storing the file in the hard disc HD by the image controller 93. In the example shown in FIG. 7, a time interval from a time point of initiating loading of a predetermined wafer W (e.g., wafer $W_2$) into a predetermined process chamber PM to a time point of completing unloading the wafer W therefrom is set as the accumulation time. In addition, it is assumed that a transfer error occurs while the wafer $W_2$ is unloaded (replaced with a succeeding wafer $W_3$). Specifically, after the unprocessed wafer $W_2$ is moved and mounted in a predetermined process chamber PM, the gate valve GP is closed, substrate processing is performed, and the substrate processing is terminated, the gate valve GP is opened and the processed wafer $W_2$ is moved and mounted on the lower arm LVA but the wafer W is misaligned and thus an abnormality occurs in the detection by the wafer detection sensor ST.

In response to the above situation, the image controller 93 reads, from the RAM 93r, the image data from the time point when the loading of the wafer $W_2$ is initiated to the time point when the detection of the abnormality in the wafer $W_2$ occurs, i.e., the time point when the transfer error occurs, among the image data of the memory areas of the RAM 93r, and converts the image data into a file. Then, the file is stored in the hard disc HD. Accordingly, the conversion into the file and the storage of the file in the hard disc HD by the image controller 93 are completed.

Hereinabove, although transfer of a wafer W in the vacuum transfer chamber TM has been described, a wafer W may also be transferred in the atmosphere transfer chamber LM in almost the same sequence.

(5) Effect According to the Present Embodiment

According to the present embodiment, one or more effects are provided as described below.

(a) According to the present embodiment, the camera CT or CL is installed for recording transfer operations by the vacuum side robot VR or the atmosphere side robot AR as image data. Thus, a state of a wafer W upon occurrence of a transfer error can be visually checked so that it becomes easy to specify an occurrence cause of the transfer error. Therefore, it becomes possible to analyze the transfer error in a short time.

(b) In addition, according to the present embodiment, detailed state information of a wafer W and substrate transfer information from the image data are displayed on the same screen. Thus, it becomes easy to specify the cause of the transfer error, making it possible to analyze the transfer error in a shorter time.

(c) Further, according to the present embodiment, there are provided the overall controller 90 for controlling transfer of a wafer W by the vacuum side robot VR and the atmosphere side robot AR and the image controller 93 for accumulating the image data recorded by the cameras CT and CL in the RAM 93r at a predetermined period of time so that if a transfer error is detected by the wafer detection sensor ST or SL or the like, the overall controller 90 provides the image controller 93 with a notification indicating that the vacuum side robot VR or the atmosphere side robot AR is stopped because of the transfer error and the image controller 93 reads, from the RAM 93r, the image data of a predetermined time interval including a time point when the transfer error occurred, converts the image data into a file, and stores the file in the hard disc HD. Accordingly, it is possible to save an effort to search for and pick up the image data when a transfer error occurs from a large amount of the image data and thus to further reduce the time required for analyzing the transfer error.

(d) Moreover, according to the present embodiment, while the image data recorded by the cameras CT and CL are overwritten at a predetermined period of time, the image data are accumulated in the RAM 93r and the image data before and after the occurrence of a transfer error are stored in the hard disc HD. In this manner, since efficiencies of collecting and storing image data in the RAM 93r or the hard disc HD are improved, it is possible to reduce a load of the RAM 93r or the hard disc HD and also to reduce a memory size of the RAM 93r or the hard disc HD.

<Second Embodiment of the Present Disclosure>

A second embodiment of the present disclosure will be described below that uses the control part CNT shown in FIG. 2 as an example. A control part CNT according to the present embodiment controls the processing parts, the transfer parts, the recording parts, the operation part, and the like in relation to the state information of a wafer W acquired from the respective components constituting the processing parts or the transfer parts. In addition, the control part CNT according to the present embodiment is different from the control part CNT of the previous embodiment in that the image data recorded by the respective cameras CT and CL and the like as the recording parts are displayed, for example, on a transfer history information screen showing transfer history information for each wafer W or a production information screen showing production information for each wafer W.

Referring to FIG. 2, the overall controller 90 installed in the control part CNT according to the present embodiment is configured such that various pieces of information concerning transfer of a wafer W by the vacuum side robot VR and the atmosphere side robot AR as the transfer parts, the gate valves GP1 to GP4 and GV1 to GV4, the vacuum load lock chambers VL1 and VL2, the wafer detection sensors ST1 to ST4, SL1, and SL2, and the like are integrated, for example, as the transfer history information for each wafer W, and the information is stored in the hard disc 90h as the first storage part.

In addition, the process chamber controllers PMC1, PMC2, . . . located in the control part CNT according to the present embodiment are configured so that various pieces of information concerning substrate processing by each of the process chambers PM1 to PM4 as the processing part having the MFC 11, the APC 12, the temperature adjuster 13, the input and output valve I/O 14, and the like are integrated, for example, as the production information indicating a substrate processing situation for each wafer W, and the information is stored in each of the hard discs 91h, 92h, . . . as the second storage parts.

Substrate processing result information is the sum of the transfer history information of a wafer W by the vacuum side robot VR, the atmosphere side robot AR, and the like and the production information indicating a substrate processing situation by the respective process chambers PM1 to PM4.

In addition, the operation part 100 installed in the control part CNT according to the present embodiment is provided with the operation screen for displaying on various screens, for example, monitoring data or various logging data indicating a state of the substrate processing apparatus 10, interpretation of an alarm, recipe editing or parameter editing. Such various screens include, for example, the transfer history information screen showing the transfer history information for each wafer W, the production information screen showing the production information for each wafer W, and the like.

Figure 15:
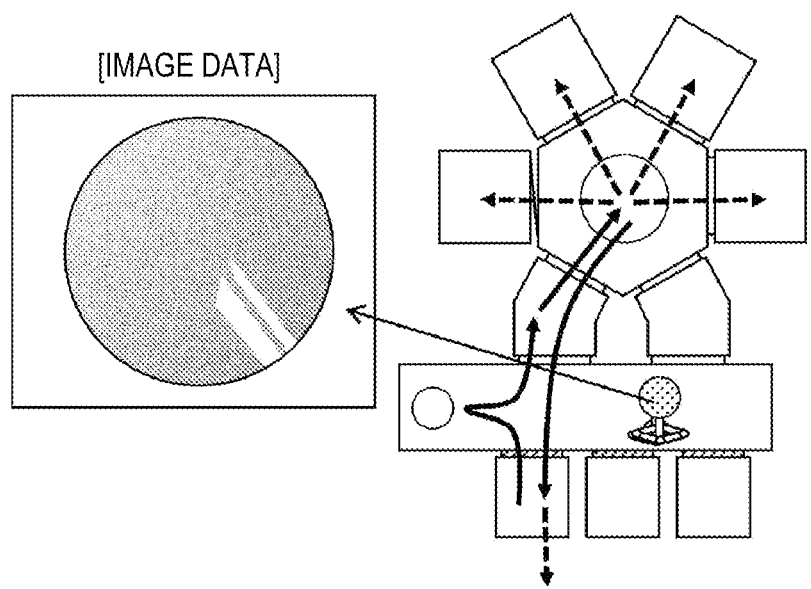
FIG. 15 shows an example of a transfer history information screen that is displayed on an operation part according to a second embodiment of the present disclosure.

The control part CNT configured as above displays the image data recorded by the cameras CT and CL and the like along with the transfer history information of a predetermined wafer W on the transfer history information screen installed in the operation part 100. FIG. 15 shows an example of the transfer history information screen that is displayed on the operation screen installed in the operation part 100.

The transfer history information screen is configured to display a transfer route of a predetermined wafer W as the transfer history information, for example, using arrows on a schematic diagram showing the substrate processing apparatus 10. In the display example of FIG. 15, the route marked with bold arrows illustrates that a predetermined wafer W is transferred from the pod PD1 held on the load port LP1 to the vacuum transfer chamber TM via an orientation flat aligner (OFA) and the vacuum load lock chamber VL1, is subjected to substrate processing in a predetermined process chamber among the process chambers PM1 to PM4, and is then unloaded to the outside of the substrate processing apparatus 10 via the same route but excluding the orientation flat aligner (OFA).

In the present embodiment, the transfer history information screen is configured to make it possible to display the image data of a wafer W at a predetermined position on the transfer route. In the display example of FIG. 15, the image data of the wafer W held on the atmosphere side robot AR in the atmosphere transfer chamber LM are displayed.

Figure 16:
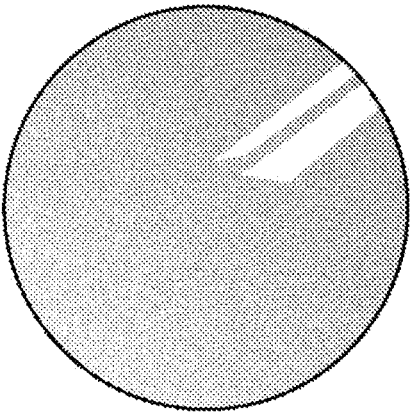
FIG. 16 shows an example of a production information screen that is displayed on the operation part according to the second embodiment of the present disclosure.

The control part CNT is also configured to display the image data recorded by the cameras CT and CL and the like along with the production information of a predetermined wafer W on the production information screen installed in the operation part 100. FIG. 16 shows an example of the production information screen that is displayed on the operation screen installed in the operation part 100.

The production information screen is configured to display, for example, a variety of states of a predetermined wafer W when it is subjected to substrate processing, as the production information. In the display example shown in FIG. 16, the production information such as pressure, temperature, and gas flow rates of the respective MFCs 11a, 11b, . . . is displayed along with production date, wafer IDs.

In the present embodiment, the production information screen is configured to make it possible to display the image data directly before and after the substrate processing of a predetermined wafer W. In the display example of FIG. 16, the image data after the substrate processing of a predetermined wafer W are displayed.

In a related art, since a state of a wafer W is confirmed only in response to abnormality detection by the wafer detection sensors SL1 and SL2, abnormality of a slot in the load ports LP1 to LP3, the production information in the substrate processing, or the like, a large amount of time or labor needs to be spent analyzing image data or specifying a cause upon the occurrence of abnormality.

However, in the present embodiment, as image data of a predetermined wafer W are displayed on the transfer history information screen or the production information screen, it is possible to easily confirm a state of the wafer W during the transfer or before and after the substrate processing. Accordingly, for example, when a crack or defect is detected in the wafer W after the wafer W is unloaded to the outside of the substrate processing apparatus 10, it is possible to easily specify whether or not the crack or defect occurred within the substrate processing apparatus 10. If it is proved that there is no crack or defect occurring within the substrate processing apparatus 10, unnecessary inspection or examination may be saved which results from suspecting abnormality of the substrate processing apparatus 10. If it is proved that the crack or defect occurs within the substrate processing apparatus 10, it is possible to rapidly specify and repair an abnormal portion of the substrate processing apparatus 10.

<Third Embodiment of the Present Disclosure>

A third embodiment of the present disclosure will be described below that uses the control part CNT shown in FIG. 2 as an example. The control part CNT according to the present embodiment is provided with the image controller 93 as an image control part, which is different in function from the second control part according to the previous embodiments. Specifically, while the previous second control part mainly stores only the image data in the hard disc HD upon occurrence of a transfer error, the image controller 93 of the present embodiment is configured to store further image data, in addition to the image data upon occurrence of a transfer error, in the hard disc HD. Accordingly, it is possible to prevent important data from being omitted, to analyze an aging change of the transfer part, and the like.

Figure 13:
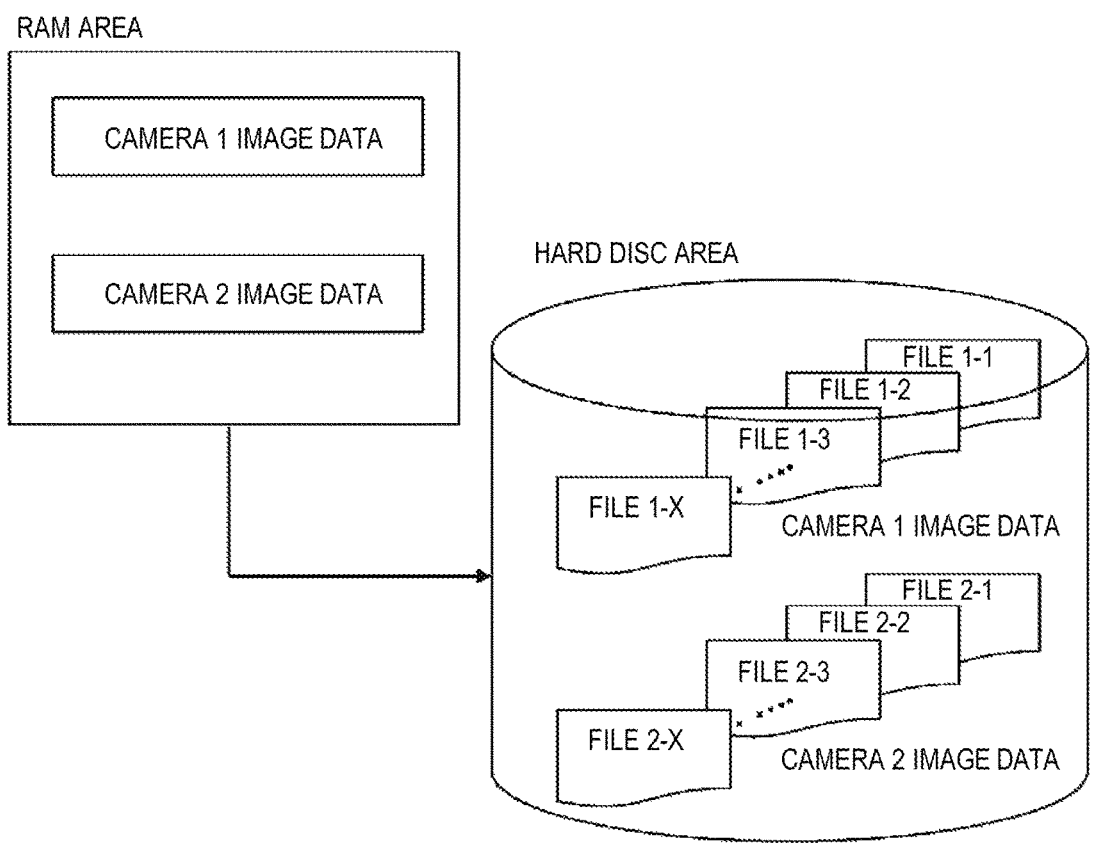
FIG. 13 shows an example of managing respective areas in a RAM and a hard disc of an image controller according to a third embodiment of the present disclosure.

The configurations of the respective areas of the RAM 93r as the accumulation part provided in the image controller 93 and the hard disc HD as the memory part are shown in FIG. 13. As shown in FIG. 13, predetermined capacities for image data obtained from individual cameras such as a camera 1 and a camera 2 are secured in the memory area of the RAM 93r provided in the image controller 93. The respective image data are accumulated in the memory areas for the cameras at a predetermined period of time.

In addition, an area for storing a file, into which the image data accumulated in each memory area of the RAM 93r is converted, is secured for each camera in the hard disc HD provided to the image controller 93. Such files are stored at predetermined times in the corresponding areas of the hard disc HD with the names of file 1-1, 1-2, 1-3, . . . , file 2-1, 2-2, 2-3, . . . and the like for the camera 1, the camera 2 and the like, respectively. In addition, the stored files are deleted at predetermined times in sequence of preparing or storing the files from the oldest to the newest.

The period of time at which the image data are accumulated in the RAM 93r, a timing at which a file of image data is stored in the hard disc HD, and a timing at which a file is deleted are set in advance in the program table 93p provided in the image controller 93.

A timing of converting the image data accumulated in the RAM 93r into a file and storing the file in the hard disc HD may be, for example, a timing at which a predetermined first set time is reached. For example, a regular time of every few minutes or the like may be designated as the first set time. When the first set time is reached, non-stored image data in the RAM 93r, such as image data of an amount for the first set time, are converted into a file and stored in the hard disc HD.

In addition, a timing of storage in the hard disc HD may be set to, for example, a timing at which a predetermined event occurs, or the like. For example, an event that the size or the number of non-stored image data accumulated in the RAM 93r reaches a predetermined value, an event that the substrate processing apparatus 10 is shifted to a standby state in which a wafer W is not processed or transferred, or the like may be designated as the predetermined event. If a predetermined event occurs, the non-stored image data in the RAM 93r, such as image data acquired from a time point when the last event occurs to a time point when this event occurs are converted into a file and stored in the hard disc HD.

In addition, a timing of deleting the file stored in the hard disc HD may be, for example, a timing at which a predetermined second set time is reached. For example, a regular time of every one day or the like may be designated as the second set time. In addition, a timing of deleting a file may be, for example, a timing at which a predetermined event occurs. For example, an event that the size or the number of files stored in the hard disc HD reaches a predetermined value, or an event that the image data which is converted into a file are stored in the hard disc HD may be designated as the predetermined event so that the storage and the deletion may be carried out in association with each other.

In the previous embodiments, for example, if files are not deleted but continuously stored in a hard disc, the hard disc would have a large number of files. In the present embodiment, since files in the hard disc HD are deleted at a predetermined time, the image data may be prevented from being massive, and less than a predetermined amount of data may be maintained.

Figure 14:
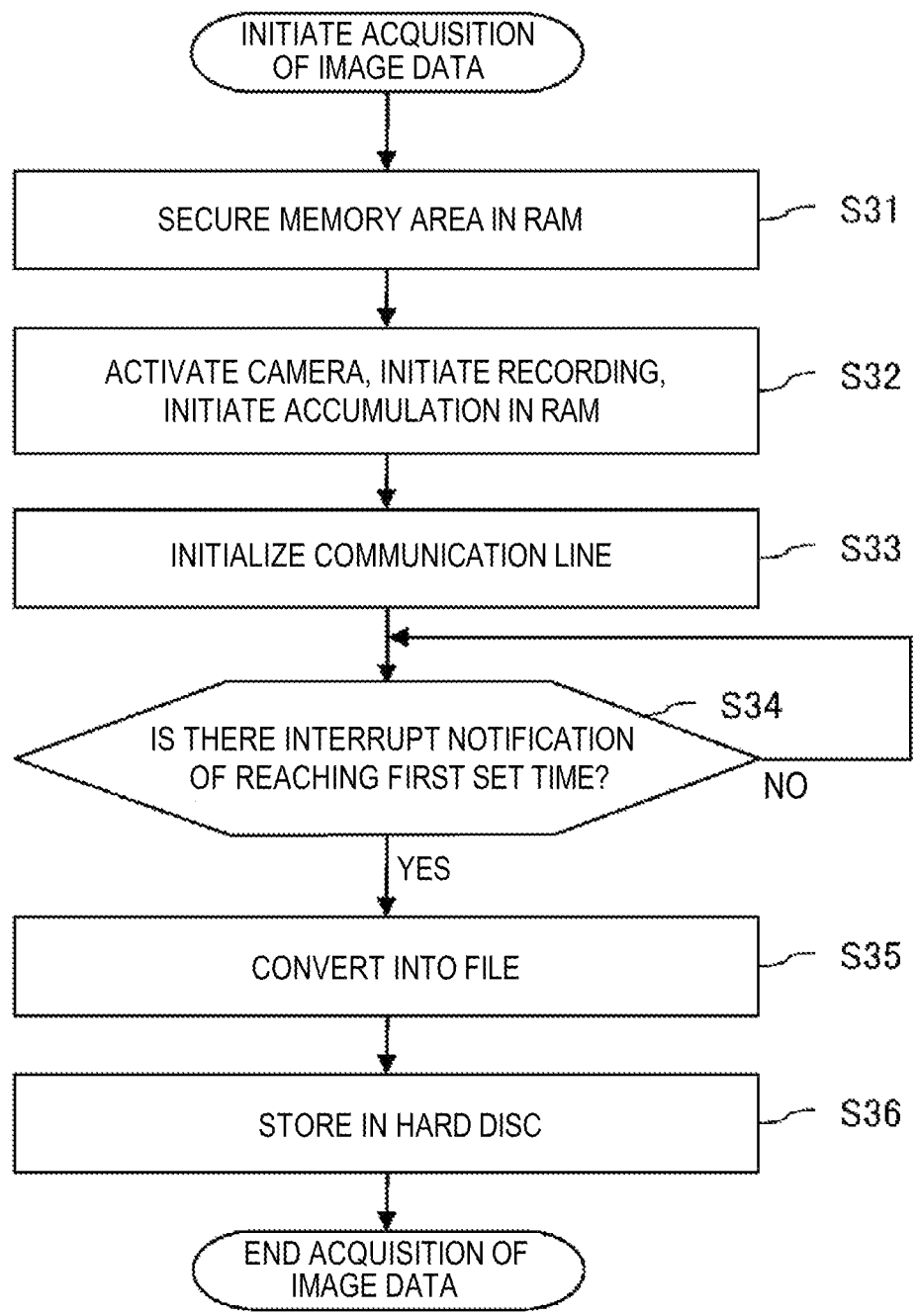
FIG. 14 illustrates a flowchart of collecting and storing image data by the image controller according to the third embodiment of the present disclosure.

The operation of the image controller 93 configured as above where the first and second set times are applied will be described with reference to FIG. 14. FIG. 14 illustrates a flowchart of collecting and storing image data by the image controller 93 according to the present embodiment.

As shown in FIG. 14, the image controller 93 performs S31 to S33 in the same sequence as S1 to S3 of FIG. 5 described above. Thereafter, while image data are accumulated in the RAM 93r at a predetermined period of time, the image controller 93 waits for an interrupt notification, for example, from a clock function or the like (not shown) (S34).

Then, for example, if the interrupt notification indicating that the first set time is reached is received (S34→"YES"), the image controller 93 stops accumulating image data in the RAM 93r, reads the accumulated image data from the RAM 93r, and converts the image data into a file (S35). The file is stored in the hard disc HD (S36). Once the storing in the hard disc HD is completed, the image controller 93 reactivates the accumulation of image data in the RAM 93r. As such, the operation of collecting and storing image data by the image controller 93 is completed.

The deletion of files stored in the hard disc HD is also performed almost in the same way as the foregoing. Specifically, for example, upon receiving the interrupt notification indicating that the second set time is reached, the image controller 93 deletes at least the oldest file among the files stored in the hard disc HD. In this case, a plurality of files including the oldest file may be selected and deleted.

In addition, when the image controller 93 is set to operate according to the occurrence of a predetermined event, the image controller 93 performs the respective predetermined operations, for example, after receiving an event occurrence notification from the overall controller 90.

In this manner, in the present embodiment, the image data including the image data on the occurrence of a transfer error are stored in the hard disc HD. Accordingly, it is possible to reduce concerns over omission of important data, for example, at a time point when a transfer error occurs. In addition, since a process of occurrence of a transfer error can be seen from the image data before and after the occurrence of the transfer error, it becomes easier to specify the cause of the transfer error. In addition, since a transfer history from normality to abnormality can be confirmed, it is possible to more surely analyze an aging change and the like.

Also, in the embodiment, files stored in the hard disc HD are deleted at a predetermined time. Accordingly, since the stored files can be kept under a predetermined amount, it is possible to relatively easily retrieve necessary data, such as the image data upon the occurrence of a transfer error. In addition, it is easier to pick up the necessary data by combining the previous embodiments by storing the image data for a predetermined time interval including a time point when the transfer error occurred as a separate file or related error information to the file including the image data upon the occurrence of the transfer error.

<Fourth Embodiment of the Present Disclosure>

A fourth embodiment of the present disclosure will be described below. In collecting and storing image data, it is possible to improve efficiencies to reduce the burden of analyzing a transfer error according to a method other than those of the previous embodiments. In the present embodiment, another method of collecting and storing image data to enable efficient analysis will be described. Also, in the present embodiment, a substrate processing apparatus having a configuration other than the previous embodiments is used.

(1) Configuration of Substrate Processing Apparatus

Figure 8:
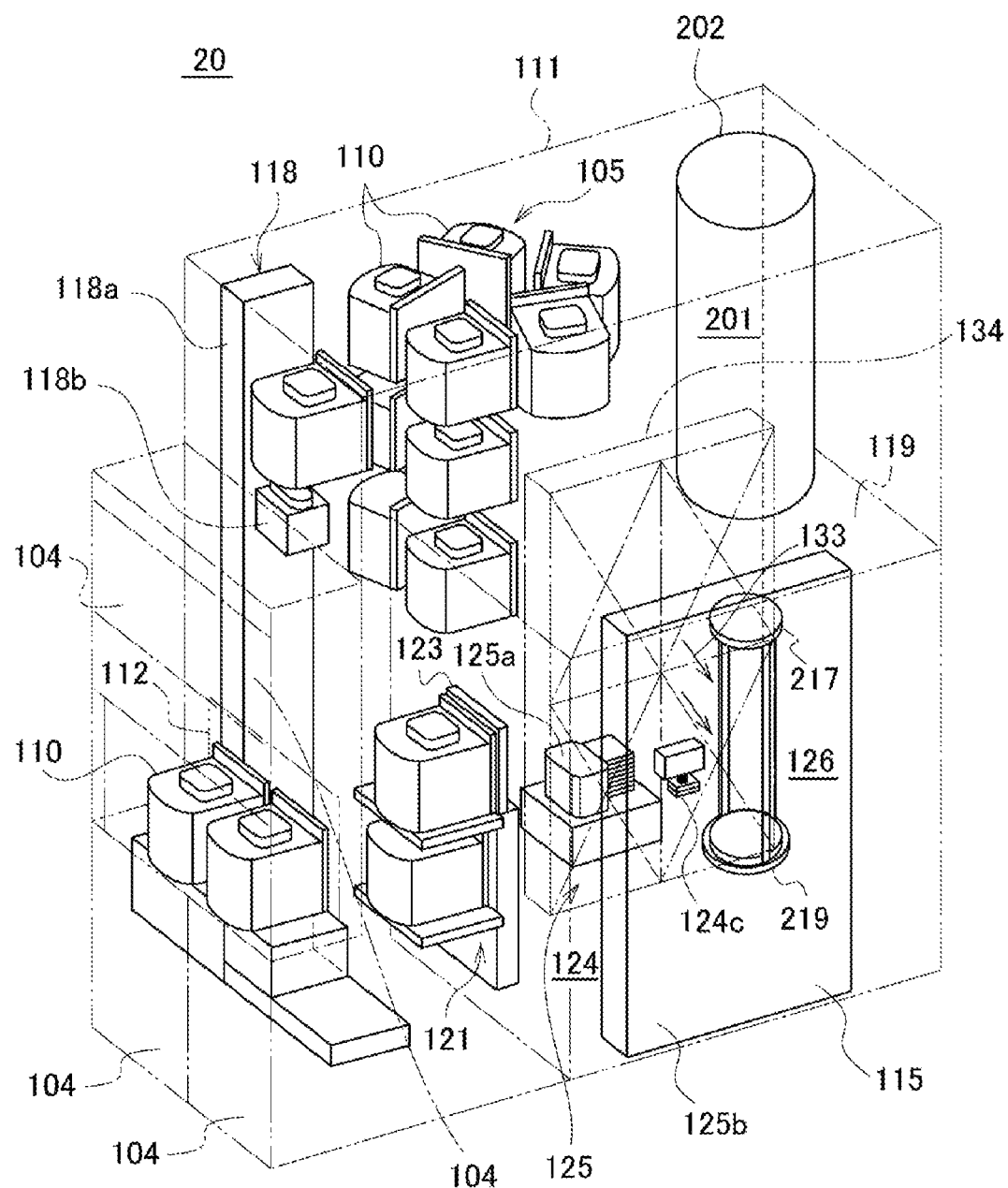
FIG. 8 illustrates a perspective view of a substrate processing apparatus according to a fourth embodiment of the present disclosure.
Figure 9:
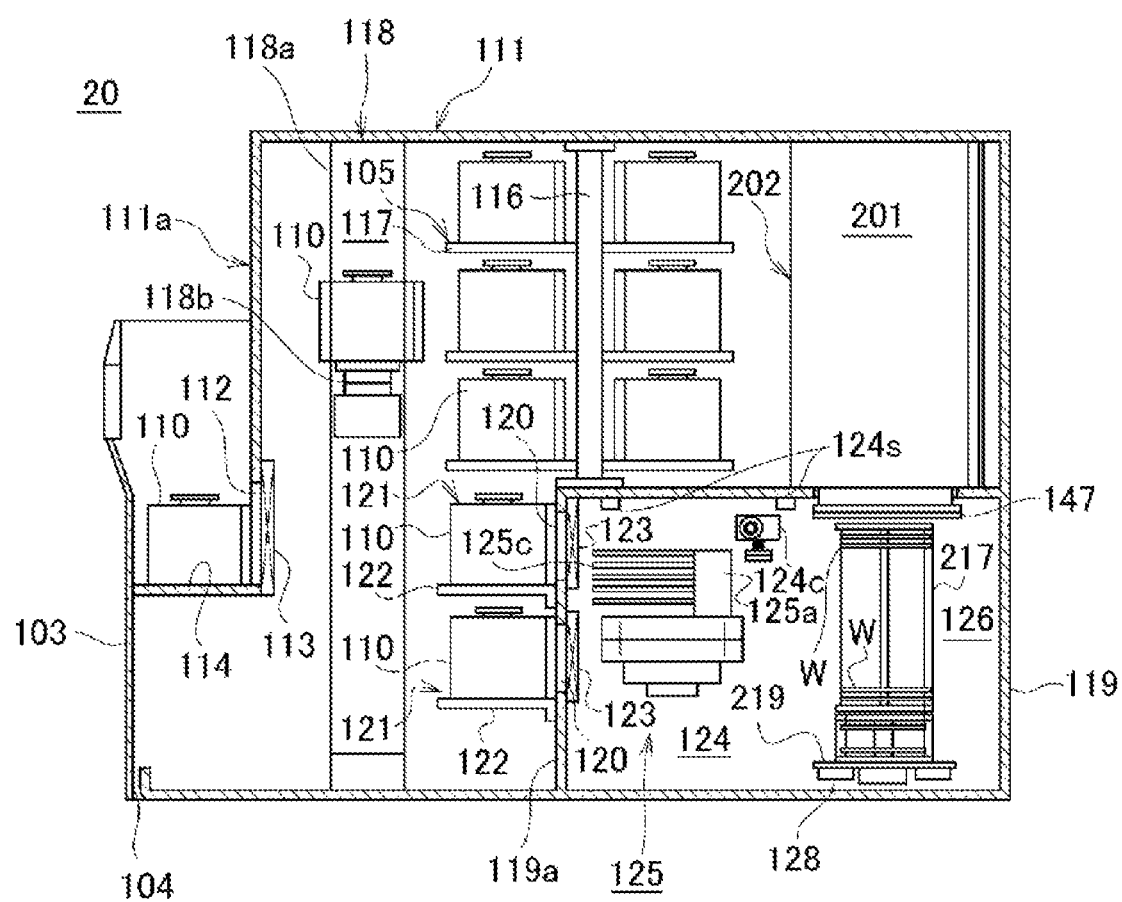
FIG. 9 illustrates a sectional view of a side of the substrate processing apparatus according to the fourth embodiment of the present disclosure.

The configuration of the substrate processing apparatus according to the fourth embodiment of the present disclosure will be described with reference to FIGS. 8 and 9. FIG. 8 illustrates a perspective view of a substrate processing apparatus 20 according to the present embodiment. In addition, FIG. 9 illustrates a sectional view of a side of the substrate processing apparatus 20 according to the present embodiment. The substrate processing apparatus 20 is configured as a vertical type substrate processing apparatus which performs, for example, oxidation processing, diffusion processing, CVD processing, or the like, to process a wafer W as a substrate made of silicon (Si) or the like.

As shown in FIGS. 8 and 9, in the substrate processing apparatus 20, FOUPs (hereinafter, referred to as pods 110) are used as substrate accommodating containers and serve as wafer carriers each accommodating wafers W. In addition, the substrate processing apparatus 20 is provided with a casing 111 configured as a pressure-resistant container.

A front maintenance port 103 used as an opening formed to enable maintenance work is installed in a front portion of a front wall 111a of the casing 111 of the substrate processing apparatus 20. Front maintenance doors 104 for opening and closing the front maintenance port 103 are located at the front maintenance port 103. In addition, a secondary operating device 237s (see FIG. 10), which will be described later, is located in the vicinity of the upper front maintenance doors 104. Also, a primary operating device 237m (see FIG. 10), which will be described later, is arranged in the vicinity of a rear maintenance door and mounted to the casing 111 to be fixed integrally with the substrate processing apparatus 20.

A pod loading/unloading port (i.e., substrate accommodating container loading/unloading port) 112 is located in the front wall 111a of the casing 111 so that the inside and the outside of the casing 111 are in communication with each other. The pod loading/unloading port 112 is configured to be opened and closed by a front shutter (i.e., opening/closing mechanism of the substrate accommodating container loading/unloading port) 113.

A load port (i.e., substrate accommodating container transfer table) 114 is located in front of the pod loading/unloading port 112. The load port 114 is configured to hold the pod 110 and align its position. The pod 110 is loaded on the load port 114 and unloaded from the load port 114 by an in-process transfer device (not shown).

A rotary pod shelf (i.e., substrate accommodating container mounting shelf) 105 is installed in an upper portion of the casing 111 at an approximately central portion in a back-and-forth direction. The rotary pod shelf 105 is configured to store a plurality of the pods 110. Specifically, the rotary pod shelf 105 is provided with a support pole 116, which is vertically erected and intermittently rotated in a horizontal plane, and a plurality of shelf plates (i.e., substrate accommodating container mounting table) 117, which are radially supported at respective positions of upper, middle, and lower stages of the support pole 116. The plurality of pods 110 is mounted and held on the plurality of shelf plates 117, respectively.

A pod transfer device (i.e., substrate accommodating container transfer device) 118 is installed between the load port 114 and the rotary pod shelf 105 in the casing 111. The pod transfer device 118 includes a pod elevator (i.e., substrate accommodating container elevation mechanism) 118a capable of holding and elevating the pod 110 and a pod transfer mechanism (i.e., substrate accommodating container transfer mechanism) 118b. The pod transfer device 118 is configured to transfer the pod 110 between the load port 114, the rotary pod shelf 105, and pod openers (i.e., opening/closing mechanism of a substrate accommodating container lid member) 121 which will be described later, by sequential operations of the pod elevator 118a and the pod transfer mechanism 118b.

A sub-casing 119 is located in a lower portion of the casing 111 extending from an approximately central portion of the casing 111 to a rear end thereof in a back-and-forth direction. A pair of wafer loading/unloading ports (i.e., substrate loading/unloading ports) 120 for loading and unloading a wafer W into and from the sub-casing 119 are located in a front wall 119a of the sub-casing 119 as upper and lower stages in a vertical direction. A pair of the pod openers 121 is located in the upper and lower wafer loading/unloading ports 120, respectively. Each pod opener 121 includes a mounting table 122 for holding the pod 110, and a cap attaching/detaching mechanism (i.e., lid member attaching/detaching mechanism) 123 for attaching and detaching a cap (i.e., lid member) of the pod 110. The pod opener 121 is configured to open and close a wafer entrance of the pod 110 by attaching and detaching the cap of the pod 110 held on the mounting table 122 by the cap attaching/detaching mechanism 123.

A delivery chamber 124 is formed by the sub-casing 119 so as to be fluidly isolated from the space where the pod transfer device 118 and the rotary pod shelf 105 are installed. A wafer transfer mechanism (i.e., substrate transfer mechanism) 125 as a transfer part is located in a front side area of the delivery chamber 124. The wafer transfer mechanism 125 includes a wafer transfer device (i.e., substrate transfer device) 125a capable of horizontally rotating or straightly moving a wafer W and a wafer transfer device elevator (i.e., substrate transfer device elevation mechanism) 125b for lifting and lowering the wafer transfer device 125a. As schematically shown in FIG. 8, the wafer transfer device elevator 125b is installed between a right side end of the casing 111 and a right side end in a front area of the delivery chamber 124 of the sub-casing 119. Using tweezers (i.e., substrate holders) 125c of the wafer transfer device 125a as mounting parts of wafers W, the wafers W are charged into and discharged from a boat (i.e., substrate holding part) 217, which will be described later, by sequential operations of the wafer the wafer transfer device 125a and transfer device elevator 125b.

Wafer detection sensors 124s as detection parts for detecting whether or not there is a wafer W are installed at respective predetermined positions of front sides of the wafer loading/unloading ports 120 and a front side of the boat 217 which waits in a waiting portion 126, which will be described later, so as to detect the presence of a wafer W on the tweezer 125c of the wafer transfer device 125a. In addition, although not shown, a mapping sensor (i.e., wafer detection sensor) for detecting a state of a wafer W charged into the boat 217 may be installed.

In addition, a camera 124c is installed in the delivery chamber 124 as a recording part, such as a compact video camera or a web camera, for recording a transfer operation by the wafer transfer mechanism 125 as image data, such as still or moving image data. In some embodiments, a plurality of the cameras 124c may be installed. Specifically, they may be installed at a plurality of positions in the delivery chamber 124, where the movement or transfer of a wafer W can be easily detected, such as respective front upper positions of the wafer loading/unloading ports 120 and the boat 217 waiting in the waiting portion 126.

The waiting portion 126 is provided in a rear side area of the delivery chamber 124 to accommodate the boat 217 and allow it to wait. A processing furnace 202 is installed in an upper portion of the waiting portion 126. A lower end of the processing furnace 202 is configured to be opened and closed by a furnace port shutter (i.e., furnace port opening/closing mechanism) 147 and to enable substrate processing in a processing chamber 201 defined inside the processing furnace 202.

As schematically shown in FIG. 8, a boat elevator (i.e., substrate holding part elevation mechanism) 115 for lifting and lowering the boat 217 is installed between the right side end of the casing 111 and a right side end of the waiting portion 126 of the sub-casing 119. A seal cap 219 as a lid member is horizontally installed at an arm 128 as a connection part that is connected to an elevation table of the boat elevator 115. The seal cap 219 is configured to vertically support the boat 217 and allow the lower end of the processing furnace 202 to be closed.

The boat 217 is provided with a plurality of holding members and is configured to horizontally hold a plurality of wafers 200 (for example, about 50 to 125 wafers) a state of being arranged in the vertical direction with their centers aligned.

In addition, as schematically shown in FIG. 8, a dean part 134 including a supply fan and a dustproof filter is installed at a left side end of an opposite side to the wafer transfer device elevator 125b and the boat elevator 115 of the delivery chamber 124, so as to supply clean air 133 such as clean atmosphere or inert gas. A notch aligner as a substrate position correction device (not shown) for position-aligning a wafer W in its circumferential direction is installed between the wafer transfer device 125a and the clean part 134. When a wafer W is an orientation flat type, an orientation flat aligner may be installed as the substrate position correction device.

After the clean air 133 ejected from the clean part 134 circulates in the notch aligner, the wafer transfer device 125a, and the boat 217 in the waiting portion 126, the clean air 133 is sucked by a duct (not show to be discharged to the outside of the casing 111, or circulates to reach a primary side (supply side) which is a suction side of the clean part 134 and is ejected again into the delivery chamber 124 by the clean part 134.

(2) Configuration of Primary Control Part

Figure 10:
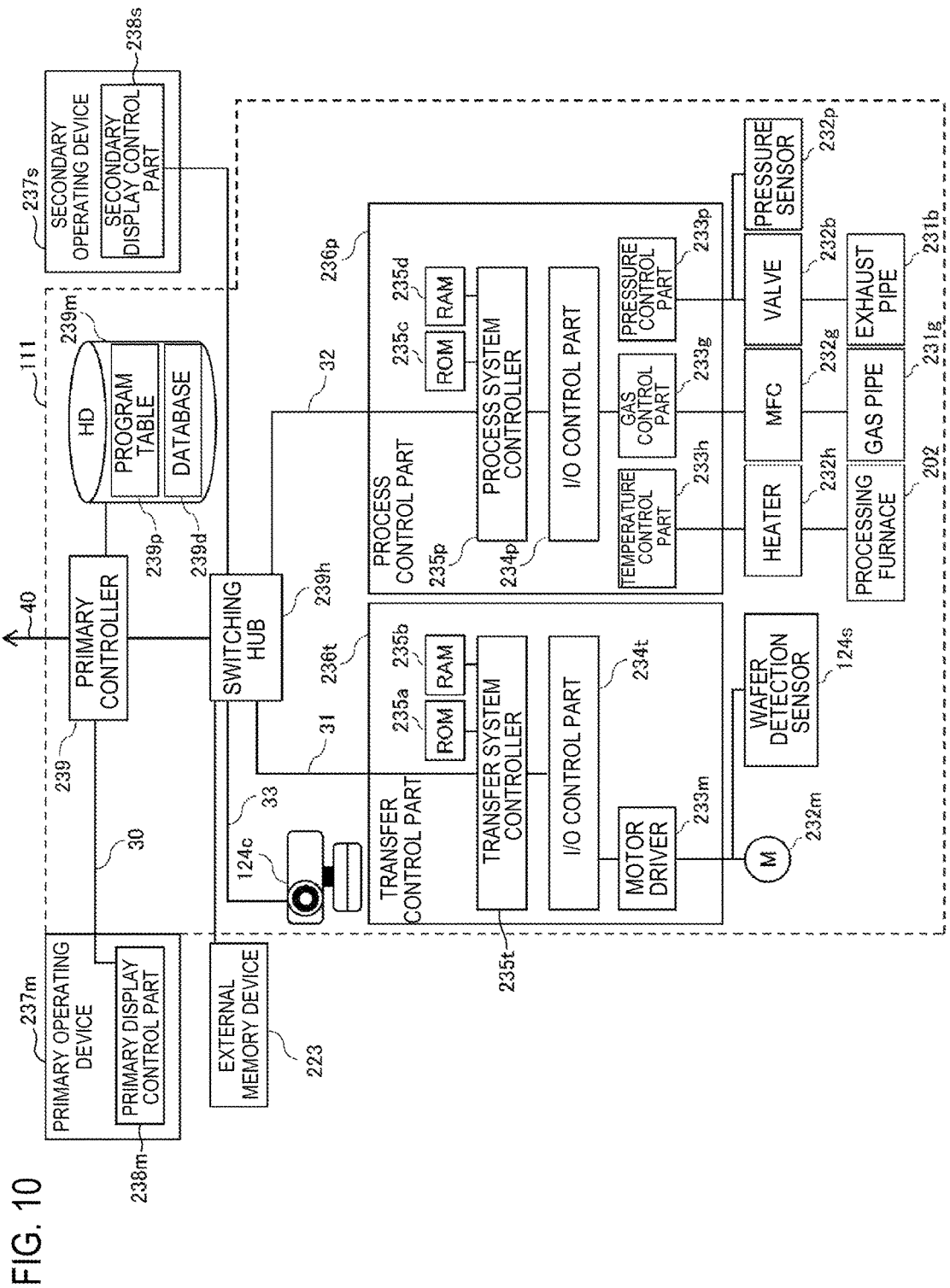
FIG. 10 shows a block diagram of an example of a schematic configuration of hardware including a primary controller of the substrate processing apparatus according to the fourth embodiment of the present disclosure.

A hardware configuration that focuses on a primary controller 239 as a primary control part for controlling the substrate processing apparatus 20 will be described with reference to FIG. 10. FIG. 10 illustrates a block diagram of an example of a schematic configuration of the hardware including the primary controller 239 of the substrate processing apparatus 20.

As shown in FIG. 10, a transfer control part 236t as a transfer control part and a process control part 236p as a substrate processing control part, in addition to the primary controller 239 and a switching hub 239h, are installed inside the casing 111 of the substrate processing apparatus 20. In addition, the camera 124c as the above-described recording part is included inside the casing 111. The transfer control part 236t and the process control part 236p may be installed outside the casing 111, instead of being installed inside the casing 111.

The primary operating device 237m is mounted to the outside of the casing 111 of the substrate processing apparatus 20, for example, to the rear side of the casing 111. In addition, by being connected to the primary controller 239 via the switching hub 239h, the secondary operating device 237s is arranged in the vicinity of the casing 111.

(Primary Controller)

The primary controller 239 as a primary control part is installed inside the casing 111 of the substrate processing apparatus 20 and is connected to the variety of control systems such as the transfer control part 236t and the process control part 236p via the switching hub 239h so as to control the respective components of the substrate processing apparatus 20. In addition, the primary controller 239 is connected to a communication network 40 such as a LAN and to an external upper level computer (not shown). Therefore, for example, for the substrate processing apparatus 20 installed in a clean room or the like in a semiconductor device manufacturing factory, the upper level computer may be installed in a place other than the clean room, such as an office. Also, in some cases, through the high level computer, another substrate processing apparatus and the like may be connected.

In addition, for example, the camera 124c installed in the delivery chamber 124 is connected to the primary controller 239 through a communication network 33 such as a LAN. Also, the primary controller 239 is provided with a hard disc (HD) 239m as a memory part for storing image data, such as still or moving image data, recorded by the camera 124c. The hard disc 239m is configured to store not only a program table 239p having storage conditions of the image data and the like defined therein and a database 239d for storing predetermined image data but also a program performing a variety of functions on the primary controller 239, recipe data of a substrate processing process performed in the processing furnace 202, data read from the substrate processing apparatus 20 by the various control parts, and the like. The program includes, for example, a control program for controlling the operation of the substrate processing apparatus 20 through the primary controller 239. The control program is readably stored in the hard disc 239m.

Once the primary controller 239 is activated, the primary controller 239 reads the program table 239p and also activates the camera 124c to initiate recording of image data. In addition, the image data, which are divided based on a predetermined time period or a time period between predetermined events according to the storage conditions of the program table 239p and the like, are converted into a file and storing the image data in the hard disc 239m is initiated. The predetermined time period or the time period between the events for dividing the image data may be set in advance. The predetermined time period may include, for example, a time period between specific time points. The time period between the events may include a time period from a loading initiation event of a wafer W into the delivery chamber 124 to an unloading termination event, a time period from a charge event of a wafer W into the boat 217 by the wafer transfer mechanism 125 to a discharge event, and the like.

In addition, the primary controller 239 selects any file including the image data acquired in a normal state in which no transfer error is detected, associates the file to information including time data indicating a time point at which the image data included in the file are acquired, a recipe content upon the acquisition of the image data, and monitoring data indicating a state of the substrate processing apparatus 20 upon the acquisition of the image data, and stores the file in the database 239d provided in the hard disc 239m. In the above-described operation, a file including the image data acquired at a predetermined time point may be designated in advance so that the file is selected. The image data which is designated in advance may be acquired, for example, when a test transfer is performed in the substrate processing apparatus 20, when instructions of acquisition of a file is inputted from the primary operating device 237*m* or the like by an operator, when a predetermined time point is reached, when a predetermined event occurs, or the like. Also, when the image data are acquired at each of those time points, numerical data including the position and velocity of the wafer transfer mechanism 125 at that time point are acquired from the transfer control part 236*t* and stored along with the files in the database 239*d*.

In addition, if a transfer error is detected by the wafer detection sensors 124*s*, the primary controller 239 causes the transfer control part 236*t* to stop the transfer part and generates error information, which includes an error notification indicating the occurrence of the transfer error, time data indicating the occurrence time of the transfer error, a recipe content upon the occurrence of the transfer error, and monitoring data upon the occurrence of the transfer error.

Figure 11:
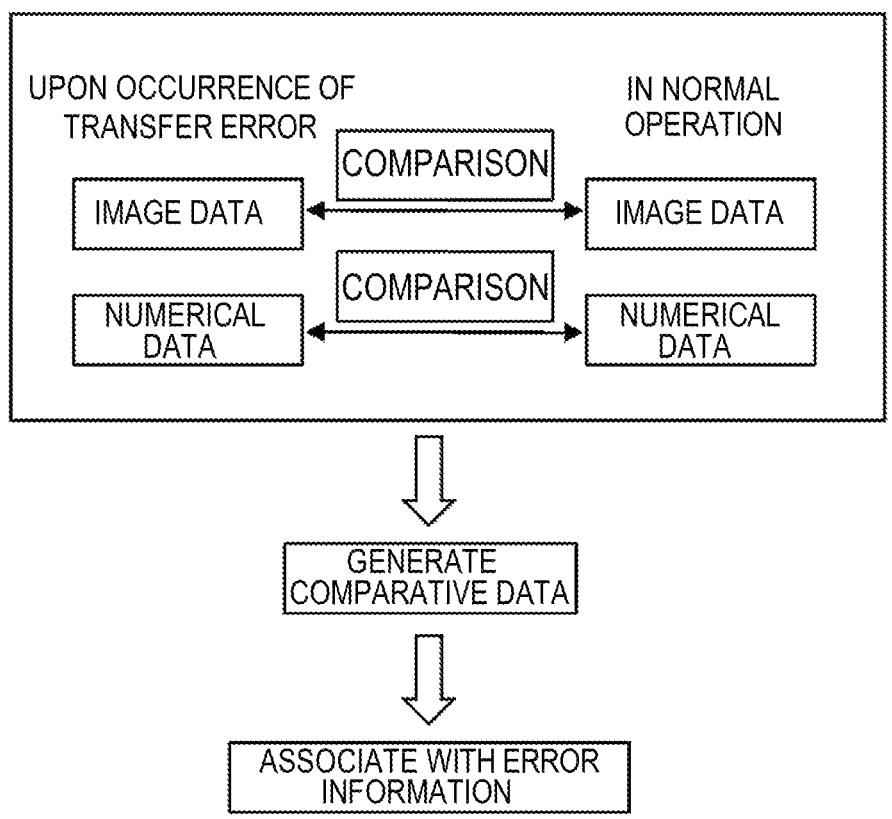
FIG. 11 illustrates an overview diagram of generating comparative data by the primary controller of the substrate processing apparatus according to the fourth embodiment of the present disclosure.

In addition, among the files stored in the hard disc 239*m*, the primary controller 239 associates the file including the image data upon the occurrence of the transfer error with the error information while also associating the numerical data including the position and the velocity of the wafer transfer mechanism 125 upon the occurrence of the transfer error with the error information. In addition, as shown in FIG. 11, the primary controller 239 compares the image data and the numerical data in a normal state pre-stored in the database 239*d* of the hard disc 239*m* with the image data and the numerical data upon the occurrence of the transfer error, generates comparative data obtained by extracting differences between these data, and associates the comparative data with the error information.

In addition, the primary controller 239 stores, in the database 239*d* installed in the hard disc 239*m*, the error information, and the file, the numerical data, and the comparative data which are associated with the error information.

Figure 12:
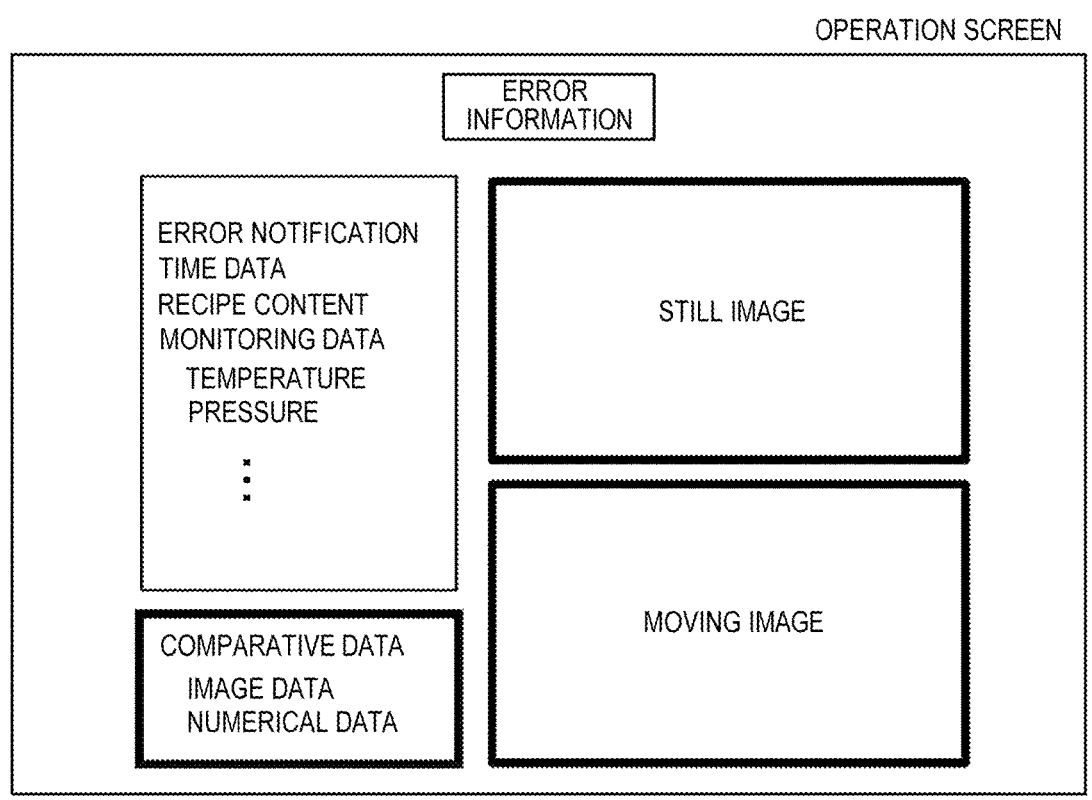
FIG. 12 shows a display example of an operation screen of the substrate processing apparatus according to the fourth embodiment of the present disclosure.

In addition, the primary controller 239 displays the error information on the operation screen installed in the primary operating device 237*m* or the secondary operating device 237*s*. In this case, the file including the image data or the numerical data in a normal state may be displayed in addition to the file, the numerical data, and the comparative data associated with the error information. A display example of the operation screen is shown in FIG. 12. The image data recorded by the camera 124*c* may be displayed on the operation screen appropriately.

The storage conditions, such as the number of the cameras 124*c*, whether or not the activation thereof is needed, a time period for dividing image data when the image data are converted into a file, and a time when image data or numerical data in a normal state are acquired, are defined in the program table 239*p* provided in the hard disc 239*m*. The primary controller 239 reads those storage conditions from the program table 239*p* to acquire or store the image data and the like.

In addition, the database 239*d* installed in the hard disc 239*m* readably stores the error information, the file, the numerical data, and the comparative data which are associated with the error information, the image data and the numerical data in a normal state, and the like, which are described above.

In addition, the program table 239*p*, which functions as a program, is a combination to cause the primary controller 239 to perform predetermined sequences for automatic transfer processing of the substrate processing apparatus 20 and to obtain predetermined results, which will be described later. Hereinafter, the program table 239*p*, the above-described control program, and the like are also collectively referred to simply as a program. In addition, the term "program" used herein includes a case in which the program includes solely the program table 239*p*, a case in which the program includes solely the control program, or a case in which the program includes both of them.

(Primary Operating Device and Secondary Operating Device)

A primary display control part 238*m* for controlling display of a primary operation screen (not shown) including a liquid crystal display panel or the like installed in the primary operating device 237*m* is installed inside the primary operating device 237*m*. The primary display control part 238*m* is connected to the primary controller 239, for example, using a video cable 30. A secondary display control part 238*s* for controlling display of a secondary operation screen (not shown) including a liquid crystal display panel or the like installed in the secondary operating device 237*s* is installed inside the secondary operating device 237*s*. The secondary display control part 238*s* is connected to the primary controller 239 via the switching hub 239*h*. Instead of using the video cable, a communication network such as a LAN may be used in such connection.

(Process Control Part)

The process control part 236*p* as a substrate processing control part has a process system controller 235*p*, for example, including a CPU or the like. The process system controller 235*p* is connected to the primary controller 239 via the switching hub 239*h* by a communication network 32 such as a LAN.

In addition, the process system controller 235*p* has a read-only memory (ROM) 235*c*, a random-access memory (RAM) 235*d*, sub-controllers (a temperature control part 233*h*, a gas control part 233*g*, a pressure control part 233*p*), and an I/O control part 234*p* for performing I/O control with the sub-controllers. The process system controller 235*p* outputs control data (e.g., control instructions) upon the processing of a wafer W to the temperature control part 233*h*, the gas control part 233*g*, and the pressure control part 233*p*, for example, based on a recipe that is prepared or edited on the primary operation screen of the primary operating device 237*m* or the like and stored in the RAM 235*d* or the like.

The ROM 235*c* or the RAM 235*d* stores sequence programs, a plurality of recipes, input data (e.g., input instructions) inputted from the primary operating device 237*m* or the like, commands of the recipes, history data upon the performance of the recipes, and the like. In addition, the process control part 236*p* may include a memory device (not shown) implemented by a hard disc HD or the like, and in this case, the memory device stores the same data as the data stored in the RAM 235*d*.

The temperature control part 233*h* controls the temperature in the processing furnace 202 by controlling output of a heater 232*h* installed in an outer peripheral portion of the above-described processing furnace 202. The gas control part 233*g* controls a supply amount or the like of process gas supplied into the processing furnace 202 based on an output value from a mass flow controller (MFC) 232*g* installed at a gas pipe 231*g* of the processing furnace 202. The pressure control part 233*p* controls a pressure in the processing furnace 202 by opening and closing a valve 232*b* based on an output value of a pressure sensor 232*p* installed at an exhaust pipe 231*b* of the processing furnace 202.

(Transfer Control Part)

The transfer control part 236t as a transfer control part has a transfer system controller 235t, for example, including a CPU or the like. The transfer system controller 235t is connected to the primary controller 239 via the switching hub 239h by a communication network 31 such as a LAN.

In addition, the transfer system controller 235t has a read-only memory (ROM) 235a, a random-access memory (RAM) 235b, a motor driver 233m, and an I/O control part 234t for performing I/O control with the motor driver 233m. The transfer system controller 235t outputs, to the motor driver 233m, control data (e.g., control instructions) upon transfer of a wafer W, for example, based on a recipe that is prepared or edited on the primary operation screen of the primary operating device 237m or the like and stored in the RAM 235b or the like. The motor driver 233m controls the transfer of a wafer W in the substrate processing apparatus 20 by a motor 232m used as a driving source for transferring the wafer W while obtaining output values of various sensors installed at the respective components of the substrate processing apparatus 20, such as the wafer detection sensors 124s installed to the delivery chamber 124.

In addition, the primary controller 239, the process control part 236p, the transfer control part 236t, or the like is not limited to a case in which it is configured as a dedicated computer but may be configured as a general-purpose computer having a central processing unit (CPU), a random access memory (RAM), a memory device, and I/O ports. For example, the primary controller 239 or the like according to the present embodiment may be configured by preparing an external memory device 223 (for example, a magnetic tape, a magnetic disc such as a flexible disc or hard disc, an optical disc such as a CD or DVD, a magneto-optical disc such as an MO, or a semiconductor memory such as a USB memory or memory card) for storing the above-described programs, installing the programs in the general-purpose computer using the external memory device 223, and the like. In this case, the primary controller 239, the process control part 236p, the transfer control part 236t, and the like may be configured as separate computers, respectively, or some of them may be integrated in a single computer. In addition, a part for supplying a program to a computer is not limited to a case in which the supply is performed through the external memory device 223. For example, the programs may be supplied not through the external memory device 223 but using a communication part such as the internet or a dedicated line. In addition, the hard disc 239m provided in the primary controller 239, the external memory device 223 or the like is configured as a computer-readable recording medium. Hereinafter, they are collectively referred to simply as a recording medium. In addition, the term "recording medium" used herein may include a case in which the recording medium includes solely the hard disc 239m, a case in which the recording medium includes solely the external memory device 223, or a case in which the recording medium includes both of them. In addition, the hard disc 239m may be configured as not only a hard disk drive (HDD) as described above but also, for example, a flash memory or the like.

(3) Operation of Substrate Processing Apparatus

Operations of the substrate processing apparatus 20 will be described below. Also, in the following descriptions, operations of the respective components of the substrate processing apparatus 20 are controlled by the control system that focuses on the primary controller 239. The operations and controls are performed as one of the semiconductor device manufacturing processes, while some others are performed as one of the data analysis processes of a transfer error.

(Activation of Primary Control Part)

If the primary controller 239 is activated, the primary controller 239 reads the program table 239p and initiates recording of image data by activating the predetermined camera 124c according to whether or not the activation defined in the storage conditions is needed. In addition, the storing of image data in the hard disc 239m is initiated in such a manner that the image data are divided based on a predetermined time period according to the storage conditions and converted into a file. In addition, a file including the image data acquired at a predetermined time point according to the storage conditions of the program table 239p is selected, associated with the information such as time data upon the acquisition of the image data, a recipe content, monitoring data, and the like, and stored in the database 239d together with the numerical data upon the acquisition of the image data.

(Transfer into Casing)

In the meantime, as shown in FIGS. 8 and 9, if the pod 110 is supplied to the load port 114, the pod loading/unloading port 112 is opened by the front shutter 113, and the pod 110 on the load port 114 is loaded into the casing 111 through the pod loading/unloading port 112 by the pod transfer device 118.

The loaded pod 110 is automatically transferred and delivered to the designated shelf plate 117 of the rotary pod shelf 105 by the pod transfer device 118. The pod 110 temporarily stored in the shelf plate 117 is transferred and delivered to one of the pod openers 121 from the shelf plate 117, and temporarily stored thereon. The pod 110 is then moved and mounted to the mounting table 122 by being transferred to the pod opener 121 from the shelf plate 117 or moved and mounted to the mounting table 122 by being directly transferred to the pod opener 121. Here, the wafer loading/unloading port 120 of the pod opener 121 is closed by the cap attaching/detaching mechanism 123, and the clean air 133 circulates throughout the delivery chamber 124. For example, the delivery chamber 124 is replete with nitrogen ($N_2$) gas as the clean air 133 and thus has an oxygen ($O_2$) concentration of 20 ppm or less, which is set to be significantly lower than an oxygen concentration in the casing 111 in air atmosphere.

(Transfer into Sub-Casing)

In the pod 110 held on the mounting table 122, while an end of its opening side is pressed against an edge of the opening of the wafer loading/unloading port 120 in the front wall 119a of the sub-casing 119, the cap of the pod 110 is detached by the cap attaching/detaching mechanism 123 of the pod opener 121 so that the wafer entrance is opened. A wafer W is picked up from the pod 110 through the wafer entrance by the tweezer 125c of the wafer transfer device 125a and is position-aligned in a notch aligner (not shown). Thereafter, the wafer W is loaded into the waiting portion 126 positioned at the rear of the delivery chamber 124 and charged into the boat 217. The wafer transfer device 125a, which delivers the wafer W to the boat 217, returns to the pod 110 and charges a succeeding wafer W into the boat 217.

In this manner, while charging the wafers W from one (upper or lower) of the pod openers 121 into the boat 217, the other pod 110 is transferred and mounted to the other (lower or upper) pod opener 121 from the rotary pod shelf 105 by the pod transfer device 118 and the pod 110 is opened by the pod opener 121.

(Transfer into Processing Furnace)

If a predetermined number of the wafers W are charged into the boat 217, the lower end of the processing furnace 202, which has been closed by the furnace port shutter 147, is opened by the furnace port shutter 147. Subsequently, as the seal cap 219 is lifted up by the boat elevator 115, the boat 217 holding the group of wafers W is loaded into the processing furnace 202.

After the boat 217 is loaded, the wafers W are subjected to any processing in the processing chamber 201 provided in the processing furnace 202. After the processing, the wafers W and the pod 110 are unloaded to the outside of the casing 111 in reverse order to that described above except the alignment process of the wafers W in the notch aligner (not shown).

(Operation Upon Occurrence of Transfer Error)

In the above case, if a transfer error is detected by the wafer detection sensors 124s and the like, the primary controller 239 stops the transfer part and generates error information such as an error notification, time data upon the occurrence of the transfer error, a recipe content, and monitoring data. In addition, the file including the image data upon the occurrence of the transfer error is associated with the error information while the numerical data are also associated with the error information, and stored together with the error information in the database 239d. The image data and the numerical data in a normal state are compared with the image data and the numerical data upon the occurrence of the transfer error so that comparative data are generated, associated with the error information, and stored in the database 239d.

In addition, when instructions of displaying the error information are inputted from the primary operating device 237m or the like by an operator, the primary controller 239 displays the error information on the operation screen installed in the primary operating device 237m or the secondary operating device 237s. Here, the file, the numerical data, or the comparative data associated with the error information may be displayed together, and the file or the numerical data including the image data in a normal state may also be displayed together.

The description of the substrate processing apparatus 20 according to the present embodiment and the data analysis method in a process of manufacturing a semiconductor device in the substrate processing apparatus 20 are completed.

Also, in the present embodiment, although the camera 124c is installed inside the delivery chamber 124 of the substrate processing apparatus 20 and the transfer operation by the wafer transfer mechanism 125 is recorded, a camera for recording the transfer operation by the pod transfer device 118 as a front transfer part in the casing 111 of the substrate processing apparatus 20 may be also installed. In this case, sensor(s) may be installed at any one or a plurality of positions in the casing 111 at which the motion, transfer, or the like of the pod 110 can be easily checked, such as the front of the pod loading/unloading port 112, the vicinity of the rotary pod shelf 105, and an upper position of each front of the pod openers 121. When a transfer error is detected by one or more pod detection sensors as detection parts installed at those positions, it is possible to perform the analysis of the transfer error based on the image data recorded by such camera(s).

(4) Effects of the Present Embodiment

The present embodiment provides the effects of the previous embodiments.

(a) According to the present embodiment, the primary controller 239 is installed which is configured to divide the image data recorded by the camera 124c based on a predetermined time period or a time period between predetermined events, convert the image data into a file, and store the file in the hard disc 239m. Thus, as the handling such as the storage or reading of image data becomes easy, it is possible to reduce the time for analyzing a transfer error.

(b) In addition, according to the present embodiment, if a transfer error is detected by the wafer detection sensors 124s, the primary controller 239 generates error information including an error notification, time data upon the occurrence of the transfer error, a recipe content, and monitoring data, and associates the file including the image data upon the occurrence of the transfer error with the error information while also associating the numerical data upon the occurrence of the transfer error with the error information. Accordingly, since the image data upon the occurrence of a transfer error can be easily retrieved from a large amount of image data, it is possible to further reduce the time for analyzing a transfer error.

(c) Further, according to the present embodiment, the image data and the numerical data in a normal state, which are stored in the hard disc 239m in advance, and the image data and the numerical data upon the occurrence of a transfer error are compared with each other, the comparative data obtained by extracting differences between those data are generated, and the comparative data are associated with the error information. Thus, since an abnormal position upon the occurrence of the transfer error with respect to the normal state can be easily specified, the analysis of the transfer error is even easier.

(d) Furthermore, according to the present embodiment, the error information is displayed on the operation screen of the primary operating device 237m or the secondary operating device 237s installed in the primary controller 239. In addition, here, the file or the numerical data upon the occurrence of the transfer error and the comparative data associated with the error information are displayed together. Accordingly, since it is possible to easily confirm the various pieces of information upon the occurrence of the transfer error from the operation screen, the analysis of the transfer error becomes easier.

<Additional Embodiments of the Present Disclosure>

Hereinabove, although the embodiments of the present disclosure are specifically described, the present disclosure is not limited to the above-described embodiments but may be variously modified without departing from the spirit of the present disclosure.

For example, in the above-described embodiments, the cases that several methods of collecting and storing image data are applied to the substrate processing apparatuses 10 and 20 different from each other as a single wafer type and a vertical type, but any methods of collecting and storing image data can be applied to the substrate processing apparatuses 10 and 20 described above as examples or other substrate processing apparatuses. In addition, the present disclosure is not limited to the configuration focusing on the control part CNT or the primary controller 239 described above as examples.

Also, in the above-described embodiments, the image data, in which there is recorded the transfer operation by the transfer part for transferring a wafer W, such as the vacuum side robot VR, the atmosphere side robot AR, or the wafer transfer mechanism 125, are used in the analysis of a transfer error. However, the transfer operation by the transfer part for transferring a substrate accommodating container such as a FOUP or a wafer cassette may be recorded and the recorded image data may be used to analyze a transfer error by the above-described method.

Further, in the above-described embodiments, the image controller 93 stops the accumulation of image data in the RAM 93r while a file, into which image data are converted, is stored in the hard disc HD. However, even during the storage in the hard disc HD, the accumulation of image data in the RAM 93r may continue.

In addition, the present disclosure may also be applied to a substrate processing apparatus for performing not only film formation processing for forming various films, such as oxide films, nitride films, or metal films, by a CVD method, an atomic layer deposition (ALD) method, a physical vapor deposition (PVD) method or the like, but also other substrate processing such as diffusion processing, annealing processing, oxidation processing, nitridation processing, or lithography processing. Specifically, the present disclosure may be applied to not only a film forming apparatus including a CVD apparatus using plasma but also a substrate processing apparatus, such as an annealing processing apparatus, an oxidation processing apparatus, a nitridation processing apparatus, an etching apparatus, an exposure apparatus, a development apparatus, a lithography apparatus, a coating apparatus, a drying apparatus, or a heating apparatus.

In addition, the present disclosure is not limited to a semiconductor manufacturing apparatus of processing a semiconductor wafer, such as the substrate processing apparatus according to the above-described embodiments, and may also be applied to a substrate processing apparatus, such as a liquid crystal display (LCD) manufacturing apparatus in which a glass substrate is processed.

<Aspects of the Present Disclosure>

Hereinafter, some aspects of the present disclosure will be additionally stated.

An aspect of the present disclosure provides a substrate processing apparatus, including a transfer part configured to transfer a substrate; a processing part configured to process the substrate; a detection part configured to detect a transfer error occurring when the substrate is transferred by the transfer part; a first control part configured to, if the transfer error is detected by the detection part, stop the transfer part; a recording part configured to record transfer operation of the substrate by the transfer part as image data; and a second control part configured to accumulate the image data recorded by the recording part in an accumulation part, wherein the first control part is further configured to acquire information indicating a state of the substrate from the transfer part or the processing part and provides the second control part with a notification indicating that the transfer part is stopped in response to the transfer error, and wherein the second control part is further configured to read, from the accumulation part, the image data of a predetermined time interval including a time point when the transfer error occurs and converts the image data into a file.

Specifically, the predetermined time may be the sum of time required for loading an unprocessed substrate into the processing chamber, a time for processing the substrate in the processing chamber, and a time required for unloading the processed substrate from the processing chamber.

In addition, the second control part may reactivate the accumulation of the image data in the accumulation part after the file is stored in a memory part.

Another aspect of the present disclosure provides a substrate processing apparatus, including a transfer part configured to transfer a substrate; a processing part configured to process the substrate; a recording part configured to record a transfer operation of the substrate by the transfer part as image data; an operation part configured to display on a plurality of screens; and a control part configured to control the transfer part, the processing part, the recording part, and the operation part in association with information indicating a state of the substrate, wherein the control part is further configure to include a first storage part configured to store, among substrate processing result information including transfer history information of the substrate by the transfer part and production information indicating a substrate processing situation by the processing part, the transfer history information, and a second storage part configured to store the production information among the substrate processing result information, if a screen for displaying the transfer history information is selected, display the image data recorded by the recording part together with the transfer history information on the operation part, and if a screen for displaying the production information is selected, display the image data recorded by the recording part together with the production information on the operation part.

Still another aspect of the present disclosure provides a substrate processing apparatus, including a transfer part configured to transfer a substrate; a recording part configured to record transfer operation of the substrate by the transfer part as image data; and an image control part configured to accumulate the image data recorded by the recording part in an accumulation part, wherein if a predetermined first set time is reached or a predetermined event occurs, the image control part reads the image data for the first set time or the image data for a time interval from a time when the last event occurs to a time when the current event occurs from the accumulation part, converts the image data into a file, and stores the file in a memory part, and if a predetermined second set time is reached or a predetermined event occurs, the image control part deletes the oldest file among the files stored in the memory part.

Specifically, the image control part reactivates the accumulation of the image data in the accumulation part after the file is stored in the memory part.

Still another aspect of the present disclosure provides a substrate processing apparatus, including a transfer part configured to transfer a substrate; a detection part configured to detect a transfer error occurring when the substrate is transferred by the transfer part; a transfer control part configured to control transfer of the substrate by the transfer part; a recording part configured to record transfer operation of the substrate by the transfer part as image data; and a primary control part configured to convert the image data into a file, by dividing the image data recorded by the recording part based on a predetermined time period or a time period between predetermined events, and store the file in a memory part, wherein the primary control part is further configured to generate error information including an error notification indicating occurrence of the transfer error, time data indicating a time point when the transfer error occurs, a recipe content upon the occurrence of the transfer error, and monitoring data indicating a state of the substrate processing apparatus upon the occurrence of the transfer error, associate the file including the image data upon the occurrence of the transfer error with the error information while associating numerical data including a position and a velocity of the transfer part upon the occurrence of the transfer error with the error information, associate comparative data, generated by comparing image data and numerical data in a normal state which are pre-stored in the memory part with the image data and the numerical data upon the occurrence of the transfer error and extracting differences between the data, with the error information, and display the error information on an operation screen installed in the primary control part.

Still another aspect of the present disclosure provides a data analysis method of a substrate processing apparatus, including transferring a substrate by controlling a transfer part by a first control part; processing the substrate by controlling a processing part by the first control part; and while transfer operation of the substrate by the transfer part is recorded as image data by a recording part, accumulating the image data recorded by the recording part in an accumulation part by a second control part, wherein if a transfer error is detected by a detection part when the substrate is transferred by the transfer part, the first control part acquires information indicating a state of the substrate from the transfer part or the processing part, stops the transfer part, and provides the second control part with a notification indicating that the transfer part is stopped in response to the transfer error, and wherein the second control part reads, from the accumulation part, the image data of a predetermined time interval including a time point when the transfer error occurs and converts the image data into a file.

Still another aspect of the present disclosure provides a data analysis method of a substrate processing apparatus, including transferring a substrate by a transfer part; processing the substrate by a processing part; recording transfer operation of the substrate by the transfer part as image data by a recording part; storing, among substrate processing result information including transfer history information of the substrate by the transfer part and production information indicating a substrate processing situation by the processing part, the transfer history information in a first storage part; storing the production information in a second storage part among the substrate processing result information; and displaying on a plurality of screens by an operation part, wherein the respective acts are performed in association with information indicating a state of the substrate, and wherein in the act of displaying on the plurality of screens, the image data recorded by the recording part are displayed together with the transfer history information on the operation part if a screen for displaying the transfer history information is selected, and the image data recorded by the recording part are displayed together with the production information on the operation part if a screen for displaying the production information is selected.

Still another aspect of the present disclosure provides a data analysis method of a substrate processing apparatus, including transferring a substrate by a transfer part; and while transfer operation of the substrate by the transfer part is recorded as image data by a recording part, accumulating the image data recorded by the recording part in an accumulation part by an image control part, wherein if a predetermined first set time is reached or a predetermined event occurs, the image control part reads, from the accumulation part, the image data for the first set time or the image data for a time interval from a time when the last event occurs to a time when the current event occurs, converts the image data into a file and stores the file in a memory part, and if a predetermined second set time is reached or a predetermined event occurs, the image control part deletes the oldest file among the files stored in the memory part.

Still another aspect of the present disclosure provides a data analysis method of a substrate processing apparatus, including transferring a substrate by controlling a transfer part by a transfer control part; and while transfer operation of the substrate by the transfer part is recorded as image data by a recording part, converting the image data into a file, by dividing the image data recorded by the recording part based on a predetermined time period or a time period between predetermined events, and storing the file in a memory part by a primary control part, wherein if a transfer error is detected by a detection part when the substrate is transferred by the transfer part, the primary control part generates error information including error notification indicating occurrence of the transfer error, time data indicating a time point when the transfer error occurs, a recipe content upon the occurrence of the transfer error, and monitoring data indicating a state of the substrate processing apparatus upon the occurrence of the transfer error, associates the file including the image data upon the occurrence of the transfer error along with numerical data including a position and a velocity of the transfer part upon the occurrence of the transfer error to the error information, associates comparative data, generated by comparing image data and numerical data in a normal state which are pre-stored in the memory part with the image data and the numerical data upon the occurrence of the transfer error and extracting differences between the data, with the error information, and displays the error information on an operation screen provided in the primary control part.

Still another aspect of the present disclosure provides a program causing a computer having a first control part and a second control part to perform a process of transferring a substrate by controlling a transfer part by the first control part; processing the substrate by controlling a processing part by the first control part; and while transfer operation of the substrate by the transfer part is recorded as image data by a recording part, accumulating the image data recorded by the recording part in an accumulation part by the second control part, wherein if a transfer error is detected by a detection part when the substrate is transferred by the transfer part, the first control part acquires information indicating a state of the substrate from the transfer part or the processing part, stops the transfer part, and provides the second control part with a notification indicating that the transfer part is stopped in response to the transfer error, and the second control part reads, from the accumulation part, the image data for a predetermined time interval including a time point when the transfer error occurs and converts the image data into a file.

Still another aspect of the present disclosure provides a program causing a computer to perform a process of transferring a substrate by a transfer part; processing the substrate by a processing part; recording the transfer operation of the substrate by the transfer part as image data by a recording part; storing, among substrate processing result information including transfer history information of the substrate by the transfer part and production information indicating a substrate processing situation by the processing part, the transfer history information in a first storage part; storing the production information in a second storage part among the substrate processing result information; and operating display on a plurality of screens by an operation part, in association with information indicating a state of the substrate, wherein in the act of operating display on the plurality of screens, the program causes the computer to perform a process of displaying the image data recorded by the recording part together with the transfer history information on the operation part if a screen for displaying the transfer history information is selected; and displaying the image data recorded by the recording part together with the production information on the operation part if a screen for displaying the production information is selected.

Still another aspect of the present disclosure provides a program causing a computer to perform a process of transferring a substrate by a transfer part; and while transfer operation of the substrate by the transfer part is recorded as image data by a recording part, converting the image file into a file by dividing the image data recorded by the recording part based on a predetermined time period or a time period between predetermined events, and storing the file in a memory part, wherein if a transfer error is detected by a detection part when the substrate is transferred by the transfer part, the program causes the computer to perform a process of generating error information including an error notification indicating occurrence of the transfer error, time data indicating a time point when the transfer error occurs, a recipe content upon the occurrence of the transfer error, and monitoring data indicating a state of the substrate processing apparatus upon the occurrence of the transfer error; associating the file including the image data upon the occurrence of the transfer error with the error information while associating numerical data including a position and a velocity of the transfer part upon the occurrence of the transfer error with the error information; associating comparative data, generated by comparing image data and numerical data in a normal state which are pre-stored in the memory part with the image data and the numerical data upon the occurrence of the transfer error and extracting differences between the data, with the error information; and displaying the error information on an operation screen.

Still another aspect of the present disclosure provides a non-transitory computer-readable recording medium storing a program causing a computer having a first control part and a second control part to perform a process of transferring a substrate by controlling a transfer part by the first control part; processing the substrate by controlling a processing part by the first control part; and while transfer operation of the substrate by the transfer part is recorded as image data by a recording part, accumulating the image data recorded by the recording part in an accumulation part by the second control part, wherein if a transfer error is detected by a detection part when the substrate is transferred by the transfer part, the first control part acquires information indicating a state of the substrate from the transfer part or the processing part, stops the transfer part, and provides the second control part with a notification indicating that the transfer part is stopped in response to the transfer error, and the second control part reads, from the accumulation part, the image data of a predetermined time interval including a time point when the transfer error occurs and converts the image data into a file.

Still another aspect of the present disclosure provides a non-transitory computer-readable recording medium storing a program causing a computer to perform a process of transferring a substrate by a transfer part; processing the substrate by a processing part; recording transfer operation of the substrate by the transfer part as image data by a recording part; storing, among substrate processing result information including transfer history information of the substrate by the transfer part and production information indicating a substrate processing situation by the processing part, the transfer history information in a first storage part; storing the production information in a second storage part among the substrate processing result information; and displaying on a plurality of screens by an operation part, in association with information indicating a state of the substrate, wherein in the act of displaying on the plurality of screens, the program causes the computer to perform a process of displaying the image data recorded by the recording part together with the transfer history information on the operation part if a screen for displaying the transfer history information is selected; and displaying the image data recorded by the recording part together with the production information on the operation part if a screen for displaying the production information is selected.

Still another aspect of the present disclosure provides a non-transitory computer-readable recording medium storing a program causing a computer to perform a process of transferring a substrate by a transfer part; and while transfer operation of the substrate by the transfer part is recorded as image data by a recording part, converting the image data into a file, by dividing the image data recorded by the recording part based on a predetermined time period or a time period between predetermined events, and storing the file in a memory part, wherein if a transfer error is detected by a detection part when the substrate is transferred by the transfer part, the program causes the computer to perform a process of generating error information including an error notification indicating occurrence of the transfer error, time data indicating a time point when the transfer error occurs, a recipe content upon the occurrence of the transfer error, and monitoring data indicating a state of the substrate processing apparatus upon the occurrence of the transfer error; associating the file including the image data upon the occurrence of the transfer error with the error information while associating numerical data including a position and a velocity of the transfer part upon the occurrence of the transfer error with the error information; associating comparative data, generated by comparing image data and numerical data in a normal state which are pre-stored in the memory part with the image data and the numerical data upon the occurrence of the transfer error and extracting differences between the data, with the error information; and displaying the error information on an operation screen.

INDUSTRIAL USE OF THE PRESENT INVENTION

Hereinabove, according to the present disclosure, there is provided a substrate processing apparatus that can be used in analyzing a transfer error by efficiently collecting and storing the image data concerning the substrate transfer.

EXPLANATION OF REFERENCE NUMERALS

90: overall controller (first control part);
93: image controller (second control part);
93r: RAM (accumulation part)
AR: atmosphere side robot (transfer part);
CL, CT: camera (recording part);
PM1 to PM4: process chamber (processing chamber);
SL1, SL2, ST1 to ST2: wafer detection sensor (detection part);
VR: vacuum robot (transfer part), W: wafer (substrate)

What is claimed is:
1. A substrate processing apparatus, comprising:
a transfer robot configured to transfer a substrate;
a processing chamber configured to process the substrate;
a detection sensor configured to detect a transfer error occurring when the substrate is transferred by the transfer robot;
at least one camera positioned to record transfer operations of the substrate by the transfer robot as image data; and
a controller in communication with the transfer robot, the processing chamber, the detection sensor and the at least one camera, and configured to accumulate the image data recorded by the at least one camera in an accumulation part,
wherein the controller is further configured to:
stop the transfer robot upon detection of the transfer error by the detection sensor:
terminate the accumulation of the image data;
specify a time point when the transfer error occurs;
determine a time interval for a series of operations, to which the time point of the transfer error occurring belongs, the time interval for the series of operations including time required for loading the substrate into the processing chamber, time for processing the substrate in the processing chamber, and time required for unloading the substrate from the processing chamber; and
read, from the accumulation part, image data corresponding to the time interval and convert the read image data into a file.

2. The substrate processing apparatus of claim 1, further comprising:
an operation part configured to operate display on a plurality of screens;
wherein the controller, in communication with the operation part, is further configured to:
comprise a first storage part configured to store, among substrate processing result information including transfer history information of the substrate by the transfer robot and production information indicating a substrate processing situation by the processing chamber, the transfer history information, and a second storage part configured to store the production information among the substrate processing result information,
if a screen for displaying the transfer history information is selected, display the image data recorded by the at least one camera together with the transfer history information on the operation part, the transfer history information including a transfer route of the substrate, and
if a screen for displaying the production information is selected, display the image data recorded by the at least one camera together with the production information on the operation part.

3. The substrate processing apparatus of claim 2, wherein the operation part is further configured to display on one of the plurality of screens information indicating a detailed state of the substrate and substrate transfer information from the image data.

4. The substrate processing apparatus of claim 1, wherein the controller is further configured to initiate the accumulation of the image data for a predetermined accumulation time interval at a predetermined period of time.

5. The substrate processing apparatus of claim 1, wherein the controller is further configured to, when the transfer error occurs, store only the image data before and after the transfer error occurs in a storage part.

6. The substrate processing apparatus of claim 1, wherein the at least one camera is installed at one or more positions where a scene including movement of the substrate and exchange of the substrate can be detected.

7. The substrate processing apparatus of claim 1, further comprising a transfer chamber to which the transfer robot is installed,
wherein the detection sensor is installed in front of the processing chamber in the transfer chamber.

8. The substrate processing apparatus of claim 1, further comprising a transfer chamber to which the transfer robot is installed,
wherein the at least one camera is installed at a front upper position of the processing chamber in the transfer chamber.

9. The substrate processing apparatus of claim 1, further comprising a transfer chamber to which the transfer robot is installed,
wherein the at least one camera is installed outside of the processing chamber.

10. The substrate processing apparatus of claim 1, wherein the accumulation part comprises a memory area storing the image data in accordance with an accumulation condition, and
wherein the controller is further configured to overwrite from a head of the memory area whenever a period of time in the accumulation condition comes.

11. The substrate processing apparatus of claim 1, wherein the accumulation part comprises a plurality of memory areas storing the image data in accordance with an accumulation condition, and
wherein the controller is further configured to accumulate the image data in sequence in the plurality of memory areas so as to overwrite from an initial memory area if all the memory areas are full.

12. A substrate processing apparatus, comprising:
a transfer device configured to transfer a substrate;
a detection sensor configured to detect a transfer error occurring when the substrate is transferred by the transfer device;
a transfer controller configured to control transfer of the substrate by the transfer device;
a camera positioned to record transfer operations of the substrate by the transfer device as image data; and
a primary controller in communication with the camera and configured to:
determine a time period, to which a time point of the transfer error occurring belongs, the time period being from a loading initiation event of the substrate into a delivery chamber to an unloading termination event of the substrate from the delivery chamber;
divide the image data based on the time period; and
convert image data corresponding to the time period into a file and store the file in a memory part,
wherein the primary controller is further configured to:
generate error information including an error notification indicating occurrence of the transfer error, time data indicating the time point of the transfer error occurring, a recipe content upon the occurrence of the transfer error, and monitoring data indicating a state of the substrate processing apparatus upon the occurrence of the transfer error;
associate the file including the image data corresponding to the time period with the error information;
associate numerical data including a position and a velocity of the transfer device upon the occurrence of the transfer error with the error information;
generate comparative data by comparing image data and numerical data in a normal state which are pre-stored in the memory part with the image data corresponding to the time period and the numerical data upon the occurrence of the transfer error;
associate the comparative data with the error information; and display the error information together with the associated comparative data and the associated file on an operation screen installed in the primary controller.

\* \* \* \* \*